United States Patent
Besirli et al.

(10) Patent No.: US 10,829,518 B2
(45) Date of Patent: *Nov. 10, 2020

(54) PEPTIDE COMPOSITIONS AND METHODS OF USE

(71) Applicants: ONL Therapeutics, Inc., Ann Arbor, MI (US); The Regents of the University of Michigan, Ann Arbor, MI (US)

(72) Inventors: Cagri G. Besirli, Ann Arbor, MI (US); Alexander J. Bridges, Saline, MI (US); John K. Freshley, Ann Arbor, MI (US); William A. Hunke, Middletown, DE (US); Linda L. Johnson, Ann Arbor, MI (US); Francis X. Smith, Salem, NH (US); Ethan Sylvain, Manchester, NH (US); David N. Zacks, Ann Arbor, MI (US)

(73) Assignees: ONL THERAPEUTICS. INC., Ann Arbor, MI (US); THE REGENT OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/673,513

(22) Filed: Nov. 4, 2019

(65) Prior Publication Data
US 2020/0123201 A1 Apr. 23, 2020

Related U.S. Application Data

(63) Continuation of application No. 15/570,948, filed as application No. PCT/US2016/030098 on Apr. 29, 2016, now Pat. No. 10,508,134.

(60) Provisional application No. 62/155,711, filed on May 1, 2015.

(51) Int. Cl.
| | | |
|---|---|---|
| *A61K 38/00* | (2006.01) | |
| *C07K 7/08* | (2006.01) | |
| *C07K 14/71* | (2006.01) | |
| *A61P 27/02* | (2006.01) | |

(52) U.S. Cl.
CPC .............. *C07K 7/08* (2013.01); *A61P 27/02* (2018.01); *C07K 14/71* (2013.01); *A61K 38/00* (2013.01); *Y02A 50/401* (2018.01); *Y02A 50/423* (2018.01)

(58) Field of Classification Search
None
See application file for complete search history.

(56) References Cited

U.S. PATENT DOCUMENTS

| | | |
|---|---|---|
| 6,001,962 A | 12/1999 | Ramer et al. |
| 8,343,931 B2 | 1/2013 | Zacks |
| 2007/0225217 A1* | 9/2007 | Chappell ............... A61P 27/02 514/300 |
| 2008/0280834 A1 | 11/2008 | Foster et al. |
| 2010/0226878 A1 | 9/2010 | Zacks |
| 2012/0196839 A1* | 8/2012 | Hutchinson .......... C07D 413/10 514/171 |
| 2014/0371161 A1 | 12/2014 | Koeberle |
| 2015/0265679 A1* | 9/2015 | Miller ................ A61K 31/44 424/85.5 |
| 2017/0002043 A1 | 1/2017 | Koeberle |
| 2018/0024145 A1 | 1/2018 | Sorek et al. |

FOREIGN PATENT DOCUMENTS

| | | |
|---|---|---|
| EA | 201792399 A1 | 5/2018 |
| EP | 2 403 937 B1 | 3/2010 |
| JP | H0690779 A | 4/1994 |
| JP | H08506728 A | 7/1996 |
| JP | 2008500816 A | 1/2008 |
| JP | 2008540532 A | 11/2008 |
| JP | 2009109489 A | 5/2009 |
| JP | 2011507903 A | 3/2011 |
| JP | 2014517005 A | 7/2014 |
| WO | WO 2007/064997 A2 | 6/2007 |
| WO | WO 2007/064997 A3 | 6/2007 |
| WO | WO 2013/106909 | 7/2013 |
| WO | WO-2013191352 A1 | 12/2013 |
| WO | WO 2016/178993 A1 | 5/2016 |
| WO | WO 2019/183246 A1 | 9/2019 |

OTHER PUBLICATIONS

Jeroudi A, et al., "Efficacy of adalimumab for pediatric Vogt-Koyanagi-Harada syndrome," *Ophthalmic Surg Lasers Imaging Retina*, 45(4):332-4 (2014).
Produit-Zengaffinen N, "JNK Inhibition Reduced Retinal Ganglion Cell Death after Ischemia/Reperfusion In Vivo and after Hypoxia In Vitro," *Adv Exp Med Biol*, 854:677-83 (2016).
Al-Ubaidi M, et al., "Bilateral retinal and brain tumors in transgenic mice expressing simian virus 40 large T antigen under control of the human interphotoreceptor retinoid-binding protein promoter," *J Cell Biol.*, 119(6):1681-1687 (1992).
Arroyo JG, et al., "Photoreceptor apoptosis in human retinal detachment," *Am J Ophthalmol.*, 139(4):605-10 (2005).
Besirli CG, et al., Inhibition of retinal detachment-induced apoptosis in photoreceptors by a small peptide inhibitor of the fas receptor, *Invest Ophthalmol Vis Sci.*, 51(4):2177-84 (2010).
Bourges JL, et al., "Intraocular implants for extended drug delivery: therapeutic applications," *Adv Drug Deliv Rev.*, 58(11):1182-202 (2006).
Bourne RRA, et al., "Prevalence and causes of vision loss in high-income countries and in Eastern and Central Europe: 1990-2010," *Br J Ophthalmol.*, 98:629-638 (2014).
Brown DM, et al., "Ranibizumab versus verteporfin for neovascular age-related macular degeneration," *N Engl J Med.*, 355(14):1432-44 (Oct. 5, 2006).

(Continued)

*Primary Examiner* — Jeanette M Lieb
(74) *Attorney, Agent, or Firm* — Wilson Sonsini Goodrich & Rosati

(57) ABSTRACT

Provided herein are compositions including peptides, pharmaceutical preparations thereof, and methods of preventing photoreceptor death therewith and protecting of retinal cells, including, but not limited to, photoreceptors and retinal pigment epithelium, from Fas- or TRAIL-mediated apoptosis.

22 Claims, 10 Drawing Sheets

(56) References Cited

OTHER PUBLICATIONS

Burton TC, "Recovery of visual acuity after retinal detachment involving the macula," *Trans Am Ophthalmol Soc.*, 80:475-497 (1982).

Li J-X, et al., "The B-Raf$^{V600E}$ inhibitor dabrafenib selectively inhibits RIP3 and alleviates acetaminophen-induced liver injury," *Cell Death Dis 5*, e1278 (2014).

Chien H and Dix RD, "Evidence for Multiple Cell Death Pathways during Development of Experimental Cytomegalovirus Retinitis in Mice with Retrovirus-Induced Immunosuppression: Apoptosis, Necroptosis, and Pyroptosis," *J Virol*, 86:10961-10978 (2012).

Chinskey ND, et al., "Retinal cell death and current strategies in retinal neuroprotection," *Curr Opin Ophthalmol.*, 25(3):228-233 (2014).

Cook B, et al., "Apoptotic photoreceptor degeneration in experimental retinal detachment," *Invest Opthalmol Vis Sci*, 36(6):990-996 (1995).

Cardiakidis Myers A, et al., "Retinal Function and Morphology in the Rabbit Eye after Intravitreal Injection of the TNF Alpha Inhibitor Adalimumab," *Curr Eye Res*, 39(11):1106-1116 (2014).

Bonny C, et al., "Cell-permeable peptide inhibitors of JNK: novel blockers of beta-cell death," *Diabetes*, 50(1):77-82 (2001).

Doucette LP and Walter MA, "Prostaglandins in the eye: Function, expression, and roles in glaucoma," *Ophthalmic Genet.*,12:1-9 (2016).

Du W, et al., "Targeting c-Met Receptor Overcomes TRAIL-Resistance in Brain Tumors," *PLoS One*, 9(4):e95490, 7 pages (2014).

Dunaief JL, et al., "The role of apoptosis in age-related macular degeneration," *Arch Ophthalmol.*, 120:1435-1442 (2002).

Roh M, et al., "Etanercept, a Widely Used Inhibitor of Tumor Necrosis Factor-α (TNF-α), Prevents Retinal Ganglion Cell Loss in a Rat Model of Glaucoma," *PLoS One*, 7(7):e40065 (2012).

Ghate D and Edelhauser HF, "Ocular drug delivery," *Expert Opin Drug Deliv.*, 3(2):275-87 (2006).

Gomes Dos Santos AL, et al., "Intraocular delivery of oligonucleotides," *Curr Pharm Biotechnol.*, 6(1):7-15 (2005).

Gregory MS, et al., "Opposing Roles for Membrane Bound and Soluble Fas Ligand in Glaucoma-Associated Retinal Ganglion Cell Death," *PLoS One*, 6(3):e17659 (2011).

Hassan TS, et al., "The effect of duration of macular detachment on results after the scleral buckle repair of primary, macula-off retinal detachments," *Ophthalmology*, 109(1):146-152 (2002).

Hisatomi T, et al., "Critical role of photoreceptor apoptosis in functional damage after retinal detachment," *Curr Eye Res.*, 24(3):161-172 (2002).

Huckfeldt RM, Vavvas DG., "Neuroprotection for retinal detachment," *Int Ophthalmol Clin.*, 53:105-117 (2013).

German OL, et al., "Retinoid X receptor activation is essential for docosahexaenoic acid protection of retinal photoreceptors," *J Lipid Res*, 54:2236-2246 (2013).

Jager RD, et al., "Age-related macular degeneration," *N Engl J Med.*, 358:2606-17 (2008).

Janoria KG, et al., "Novel approaches to retinal drug delivery," *Expert Opin Drug Deliv.*, 4(4):371-388 (Jul. 2007).

Ji J, et al., "Effects of elevated intraocular pressure on mouse retinal ganglion cells," *Vision Res.*, 45(2):169-179 (2005).

Jiang S, et al., "Associations of plasma-soluble fas ligand with aging and age-related macular degeneration," *Invest Ophthalmol Vis Sci.*, 49:1345-1349 (Apr. 2008).

Johnson PT, et al., "Drusen-Associated Degeneration in the Retina," *Invest Ophthalmol Vis Sci.*, 44:4481-488 (2003).

Ju KR, et al., "Retinal glial cell responses and Fas/FasL activation in rats with chronic ocular hypertension," *Brain Res.*, 1122(1):209-221 (2006).

Kanan Y, et al., "Light induces programmed cell death by activating multiple independent proteases in a cone photoreceptor cell line," *Invest Ophthalmol Vis Sci.*, 48(1):40-51 (2007).

Kamat SS, et al., "The Role of the Immune System in Glaucoma: Bridging the Divide Between Immune Mechanisms in Experimental Glaucoma and the Human Disease," *Semin Ophthalmol.*, 31(1-2):147-154 (2016).

Kim Y, et al., "DICER1/Alu RNA dysmetabolism induces Caspase-8-mediated cell death in age-related macular degeneration," *Proc Natl Acad Sci U S A*, 111:16082-16087 (2014).

Klein R and Klein BEK, "The Prevalence of Age-Related Eye Diseases and Visual Impairment in Aging: Current Estimates," *Arch Ophthalmol.*, 129:75-80 (2011).

Elsherbiny NM, et al., "ABT-702, an adenosine kinase inhibitor, attenuates inflammation in diabetic retinopathy," *Life Sci.*, 93(2-3):78-88 (Jul. 30, 2013).

Lin H, et al., "Effect of miR-23 on Oxidant-Induced Injury in Human Retinal Pigment Epithelial Cells," *Invest Ophthalmol Vis Sci.*, 52:6308-6314 (2011).

Miller JW, "Treatment of age-related macular degeneration: beyond VEGF," *Jpn J Ophthalmol.*, 54:523-528 (2010).

Miyake M, et al., "The Contribution of Genetic Architecture to the 10-Year Incidence of Age-Related Macular Degeneration in the Fellow Eye," *Invest Ophthalmol Vis Sci.*, 56(9): 5353-61 (2015).

Zhang T, et al., "Protection of photoreceptors by intravitreal injection of the Y-27632 Rho-associated protein kinase inhibitor in Royal College of Surgeons rats," *Mol Med Rep.*, 12(3):3655-61 (Sep. 2015).

Murakami Y, et al., "Photoreceptor cell death and rescue in retinal detachment and degenerations," *Prog Retin Eye Res*, 37:114-140 (2013).

Petrukhin K, "New therapeutic targets in atrophic age-related macular degeneration," *Expert Opin Ther Targets*, 11:625-639 (2007).

Rogala J, et al., "In Vivo Quantification of Retinal Changes Associated with Drusen in Age-Related Macular Degeneration," *Invest Ophthalmol Vis Sci.*, 56:1689-1700 (2015).

Ross WH, Kozy DW, "Visual recovery in macula-off rhegmatogenous retinal detachments," *Ophthalmology*, 105:2149-2153 (1998).

Tan E, et al., "Expression of Cone-Photoreceptor—Specific Antigens in a Cell Line Derived from Retinal Tumors in Transgenic Mice," *Invest Ophthalmol Vis Sci.*, (3):764-768 (2004).

Zacks DN, et al., "Caspase Activation in an Experimental Model of Retinal Detachment," *Invest Ophthalmol Vis Sci.*, 44(3):1262-1267 (2003).

Zacks DN, et al., "Role of the fas-signaling pathway in photoreceptor neuroprotection," *Arch Ophthalmol*, 125:1389-1395 (2007).

Zacks DN, et al., "Fas-Mediated Apoptosis and Its Relation to Intrinsic Pathway Activation in an Experimental Model of Retinal Detachment," *Invest Ophthalmol Vis Sci*, 45(12):4563-4569 (2004).

Zou C, et al., "Lack of Fas antagonism by Met in human fatty liver disease," *Nat Med.*, 13(9):1078-85 (Sep. 2007; Epub Aug. 19, 2007).

Wang Y, et al., "Enhanced apoptosis in retinal pigment epithelium under inflammatory stimuli and oxidative stress," *Apoptosis*, 17:1144-1155 (2012).

Yang L, et al., "Preventing Retinal Detachment—Associated Photoreceptor Cell Loss in Bax-Deficient Mice," *Invest Ophthalmol Vis Sci.*, 45(2):648-654 (2004).

International Search Report and Written Opinion received in PCT Application No. PCT/US16/30098 dated Aug. 30, 2016.

International Preliminary Report on Patentability received in PCT Application No. PCT/US16/30098 dated Nov. 7, 2017.

Wikipedia, the free encyclopedia, Amino Acids supporting document (Apr. 2015).

Cruciani, et al., "Investigation about causes of blindness and low vision among members of Blind and Visually Impaired Italian Union (UICI)," *La Clinica Terapeutica*, (2011), 162:e35-42 (Abstract).

Martin, Remington's Pharmaceutical Sciences, 15$^{th}$ Ed., Mack Publ. Co., Easton, Pa. [1975] (Title, Bibliography Page, and Table of Contents).

Reporting email dated Aug. 24, 2018 received from foreign associate enclosing an Official Action dated Aug. 2, 2018 issued by the Eurasian Patent Office in Eurasian Patent Application No. 201792399.

Official Action (and English Translation) received in Eurasian Patent Application No. 201792399 dated Aug. 2, 2018.

(56) References Cited

OTHER PUBLICATIONS

Communication regarding Extended European Search Report issued in the corresponding European Application No. EP 16 78 9830.3 dated Sep. 21, 2018, including Supplementary European Search Report dated Sep. 13, 2018.

Kim et al., "Peptide amidation: Production of peptide hormones in vivo and in vitro," *Biotechnology and Bioprocess Engineering*, 6:244-251 (2001).

Reporting email dated Mar. 18, 2019 received from foreign associate with an Official Action dated Jan. 31, 2019 issued by the Eurasian Patent Office in Eurasian Patent Application No. 201792399 and English translation of the Official Action.

Reporting email dated Jul. 10, 2019 received from a foreign associate with an Official Action dated Jun. 25, 2019 issued by the Eurasian Patent Office in Eurasian Patent Application No. 201792399, and English translation of the Official Action.

Reporting email dated Aug. 29, 2019 received from a foreign associate with an Official Action dated Aug. 15, 2019 issued by the Eurasian Patent Office in Eurasian Patent Application No. 201792399, and English translation of the Official Action.

Jiang, G., et al. "HMGB1 release triggered by the interaction of live retinal cells and uveitogenic T cells is Fas/FasL activation-dependent," *Journal of Neuroinflammation*, 12:179, DOI 10.1186/s12974-015-0389-2, 10 pages (2015).

Matsumoto, H., et al., "Membrane-bound and soluble Fas ligands have opposite functions in photoreceptor cell death following separation from the retinal pigment epithelium," *Cell Death and Disease*, 6, e1986; do1:10.1038/cddis.2015.334 (2015).

ONL Therapeutics, "ONL Therapeutics Provides Update on Novel Photoreceptor Protection Platform for Retinal Diseases," *Internet Wire*, COMTEX News Network, Inc., 3 pages (Jun. 15, 2015).

Notification of Transmittal of the International Search Report and International Search Report and Written Opinion of the International Searching Authority received in PCT Application No. PCT/US19/23207 dated Aug. 22, 2019.

Xiao, "Protective Effect of Met12, a Small Peptide Inhibitor of Fas, on the Retinal Pigment Epithelium and Photoreceptor After Sodium Iodate Injury," *Invest Ophthalmol Vis Sci*, 58:1801-1818 (2017).

\* cited by examiner

Figure I

PEPTIDE COMPOSITIONS AND METHODS OF USE

RELATED APPLICATIONS

The present patent document is a continuation application of U.S. patent application Ser. No. 15/570,948, filed Oct. 31, 2017, which is a § 371 filing based on PCT Application Serial No. PCT/US2016/030098, filed Apr. 29, 2016, which claims the benefit of the filing date under 35 U.S.C. § 119(e) of Provisional U.S. Patent Application Ser. No. 62/155,711, filed May 1, 2015, which is hereby incorporated by reference.

FEDERALLY SPONSORED RESEARCH OR DEVELOPMENT

This invention was made with Government support under Grant No. R44EY0225 I2, awarded by the National Institute of Health (NIH). The Government has certain rights in this invention.

All patents, patent applications and publications, and other literature references cited herein are hereby incorporated by reference in their entirety. The disclosures of these publications in their entireties are hereby incorporated by reference into this application in order to more fully describe the state of the art as known to those skilled therein as of the date of the invention described and claimed herein.

BACKGROUND

Peptide compositions that are protective of cells, especially retinal cells, including, but not limited to, photoreceptors, retinal pigment epithelium (RPE), and retinal ganglion cells, which receive visual information from photoreceptors, from extrinsic pathway-mediated cell death, such as Fas-mediated apoptosis, TRAIL-mediated apoptosis, TNF-mediated necroptosis, and pyroptosis, and methods of using the compositions are described.

Several major causes of vision loss, such as retinal detachment, glaucoma and macular degeneration, have a significant component of apoptotic signaling, which in turn leads to programmed cell death in certain very important types of cells in the retina. Three of these cell types are the retinal pigmented epithelial cells, where loss is seen in retinal bleaching, retinitis pigmentosa and the dry form of age-related macular degeneration, the retinal ganglionic cells, where loss is seen in glaucoma, and the photoreceptor cells themselves, the primary visual signaling cells and whose loss is the ultimate cause of vision loss from retinal diseases.

Retinal detachment (RD), defined as the separation of the neurosensory retina from subjacent RPE, results in the apoptotic death of photoreceptor cells (Cook et al. 1995; 36(6):990-996; Hisatomi et al. Curr Eye Res. 2002; 24(3): 161-172; Zacks et al. Invest Ophthalmol Vis Sci. 2003: 44(3):1262-1267. Yang et al. Invest Ophthalmol Vis Sci. 2004; 45(2):648-654; herein incorporated by reference in their entireties). Rodent and feline models of RD have demonstrated the activation of pro-apoptotic pathways nearly immediately after the retina becomes separated from the RPE (Cook et al. 1995; 36(6):990-996; Hisatomi et al. Curr Eye Res. 2002; 24(3):161-172; Zacks et al. Invest Ophthalmol Vis Sci. 2003; 44(3): 1262-1267. Yang et al. Invest Ophthalmol Vis Sci. 2004; 45(2):648-654; herein incorporated by reference in their entireties). Histological markers of apoptosis such as terminal deoxynucleotidyl transferase nick end label (TUNEL) staining reach a peak at approximately three days after RD, with apoptotic activity and progressive cell death persisting for the duration of the detachment period. This has also been validated in human retinal detachments (Arroyo et al. Am J Ophthalmol. 2005 April; 139(4):605-10). Clinical experience in the repair of retinal detachments, however, has demonstrated that there is a window of opportunity for repair with preservation of some visual acuity, but that the visual acuity drops significantly as the time between detachment and repair extends (Burton. Trans Am Ophthalmol Soc. 1982; 80:475-497; Ross et al. Ophthalmology. 1998; 105(11):2149-2153: Hassan et al. Ophthalmology. 2002; 109(1): 146-152; herein incorporated by reference in their entireties). The rapid rate of activation of pro-apoptosis pathways and the slower rate of visual loss suggests that intrinsic neuroprotective factors may become activated within the neural retina, and may serve to counter-balance the effects of the pro-apoptotic pathways activated by retinal-RPE separation.

Age-Related Macular Degeneration (AMD) is the leading cause of permanent vision loss in the United States (Bourne et al. Br J Ophthalmol. 2014; 98:629-638; Klein et al. Arch Ophthalmol. 2011; 129:75-80; Cruciani et al. Clin Ter. 2011; 162:e35-42). Death of the outer retina (defined here as the complex of retinal pigment epithelium (RPE) and photoreceptor (PR) cells) is the root cause of vision loss in AMD and limits the effectiveness of current treatments (Murakami et al, Prog Retin Eye Res. 2013; 37:114-140; Huckfeldt and Vavvas. Int Ophthalmol Clin. 2013; 53:105-117). Disruption of PR-RPE homeostasis results in PR death. Fas was significantly expressed in eyes of people with advanced AMD, defined as wet or atrophic, compared to healthy controls and was most concentrated around active neovascular and atrophic lesions (Dunaief et al. Arch Ophthalmol. 2002; 120: 1435-1442). RPE is sensitive to Fas-mediated apoptosis under stress conditions that occur during AMD progression, such as inflammation or oxidative stress, and higher concentrations of soluble Fas ligand were identified in AMD patients when compared to their age-matched healthy counterparts (Jiang et al. Invest Ophthalmol Vis Sci. 2008; 37:114-140). Similarly, oxidative stress, which occurs during AMD progression, results in the increased expression of Fas in the RPE (Lin et al. Invest Ophthalmol Vis Sci. 2011; 52:6308-6314) and the death of the RPE that occurs in conditions of oxidative stress is dependent on Fas signaling (Wang et al. Apoptosis. 2012; 17:1144-1155). Additionally, Fas has been directly linked to RPE cell death induced by Alu RNA accumulation, another recognized factor of AMD pathology (Kim et al, Proc Natl Acad Sci USA. 2014; 111:16082-16087). The TRAIL-RI receptor (DR4), which operates partially through the same pathway has been shown to be a genetic risk factor for The TRAIL-RI receptor (DR4), which operates partially through the same pathway has been shown to be a genetic risk factor for Age-related macular degeneration. (Miyake et al. Invest Ophthalmol Vis Sci 56, 5353 (2015).

Fas has also been implicated in glaucoma-associated retinal ganglion cell death (Gregory et al. PLoS One. 2011; 6(3):e17659). Furthermore, intraocular pressure (IOP) is a major risk factor for glaucoma progression, and animal models of IOP exhibit increased Fas and FasL expression (Ju et al. Brain Res. 2006; 1122(1): 209-221) and retinal ganglion cell death by apoptosis (Ji et al. Vision Res. 2005; 45(2): 169-179). While control of IOP is a main tenet of clinical treatment of glaucoma, there are a substantial number of patients that continue to experience disease progression even after proper control of IOP, and additional work has reinforced the notion that additional contributing factors to glaucoma may need to be addressed (Kamat et al. Semin Ophthalmol. 2016; 31(1-2):147-154).

Apoptosis (programmed cell death) plays a central role in the development and homeostasis of all multi-cellular organisms. Alterations in apoptotic pathways have been implicated in many types of human pathologies, including developmental disorders, cancer, autoimmune diseases, as well as neuro-degenerative disorders, and retinal degradation. It is a tightly regulated pathway governing the death processes of individual cells and can be initiated either extrinsically or intrinsically. The latter is an intracellular mechanism triggered by the mitochondria while the former involves the interaction of a 'death receptor' with its corresponding ligand at the cell membrane. Thus, the programmed cell death pathways have become attractive targets for development of therapeutic agents. In particular, since it is conceptually easier to kill cells than to sustain cells, attention has been focused on anti-cancer therapies using pro-apoptotic agents. However, there are many diseases where inappropriate activation of apoptotic pathways leads to the degeneration of tissues, and treatments have to be devised to block whichever apoptotic pathway, intrinsic or extrinsic, has been activated in this particular disease pathology.

The Fas receptor is the most common of the death receptors involved in apoptosis in degenerative diseases of the retina. (Chinsky et al. Curr Opin Ophthalmol. 2014 25(3); 228-233) Fas is a typical cytokine cell surface receptor, and is activated by trimerization when it binds to its trimeric cognate ligand FasL. Stressed retinal cells, for example photoreceptors after RD, upregulate the Fas receptor. Invading immune cells, attracted by the stress response, express the transmembrane protein Fas ligand (FasL) on their surface. FasL binds with the Fas receptors on the retinal cells, leading to a rapid activation of the extrinsic cell death pathway with signaling through the caspase cascade. Initially, the "initiator" caspase-8 is cleaved to an active form, which in turn activates caspase 3, a downstream "executioner" of the apoptotic cell death pathway. However, in the eyes of mice infected with murine cytomegalovirus, Fas, as well as the related death receptors TNFRI and TRAIL, have been shown to be activated, and this activity can lead to apoptosis, necroptosis, and pyroptosis in cells of the eye. (Chien and Dix J Virol 86, 10961 (2012))

It has been shown that photoreceptor cells in culture are very sensitive to apoptosis induced by FasL suggesting that FasL-induced apoptosis is a major contributor to vision loss in retinal diseases. (Burton. Trans Am Ophthalmol Soc. 1982; 80:475-497; Ross et al. Ophthalmology. 1998; 105 (11):2149-2153; Hassan et al. Ophthalmology. 2002; 109 (1):146-152.) Furthermore, a small peptide inhibitor of the Fas receptor, Met-12, $H^{60}HIYLGAVNYIY^{71}$ (SEQ ID NO:2) derived from the Fas-binding extracellular domain of the oncoprotein Met. (Zou et al. Nature Medicine 13, 1078 (2007) has been shown to be photoreceptor protective, both in cell culture experiments, and in the setting of separation of the retinal and retinal pigment epithelium and other ocular conditions or diseases. (Besirli et al., *Invest Ophthalmol Vis Sci.*, 51(4):2177-84 (2010); U.S. Pat. No. 8,343,931; herein incorporated by reference in their entireties). Furthermore c-Met, presumably using the same binding domain with homology to Met-12, FasL, TNAα and TRAIL has been shown to block TRAIL-induced apoptosis in various tumors. (Du et al. PLoS One 9, e95490 (2014))

The Met-12 peptide itself has biopharmaceutical properties, dominated by its extremely poor aqueous solubility. Experiments have clearly shown that Met-12 has to be dosed as a solution, both in vitro and in vivo, to show optimal activity, and producing such solutions in a largely aqueous medium has proven to be very difficult, especially under conditions which are acceptable for intravitreal injection. Dosing of suspensions or gels of Met-12 leads to major losses of potency. For example, even an apparently clear 10 rang/mL solution of Met-12 in 20 mM citrate buffer pH 2.8 showed a considerable loss of material upon filtration, and when used in both the in vitro and in vivo assays described below, led to at least a fivefold loss in activity. Despite extensive development work, the only solution formulations of Met-12 which have been found involve some very low pH solution injections (≤pH 2.8) or neat DMSO injections, all of which are suboptimal for intravitreal injections.

As such, peptide compositions that are protective of retinal cells, including, but not limited to, photoreceptors, retinal ganglionic cells and retinal pigment epithelium, from extrinsic pathway cell death, including Fas- and TRAIL-mediated apoptosis, that are easy to formulate in a solution or suspension, which can be delivered into the eye in a way to create sufficient exposure, without the use of excipients which may cause ocular (or other toxicity, and that are easy to use, are still needed to help preserve vision.

SUMMARY

Provided herein are pharmaceutical preparations of biologically active, aqueous formulations of a photoreceptor-protective peptide, pharmaceutical preparations thereof, and methods of preventing photoreceptor death therewith as well as therapeutic methods.

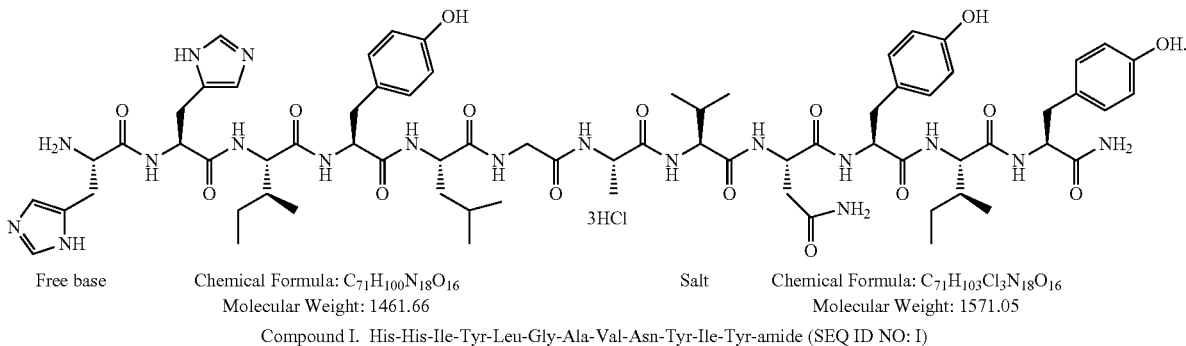

Free base  Chemical Formula: $C_{71}H_{100}N_{18}O_{16}$      Salt    Chemical Formula: $C_{71}H_{103}Cl_3N_{18}O_{16}$
Molecular Weight: 1461.66      Molecular Weight: 1571.05

Compound I. His-His-Ile-Tyr-Leu-Gly-Ala-Val-Asn-Tyr-Ile-Tyr-amide (SEQ ID NO: I)

Some embodiments relate to a C-terminal amide peptide, Compound 1 (above), or a pharmaceutically acceptable salt thereof. Certain other embodiments relate to a polyacetate salt of the Compound 1. Certain further embodiments relate to a triacetate salt of the Compound 1. The compounds may be for use in a pharmaceutical formulation for preventing Fas- or TRAIL mediated apoptosis in the photoreceptors of the eye. The compounds may be for use in a pharmaceutical formulation for preventing Fas-mediated apoptosis in cells of the retinal pigmented epithelium of the eye. The compounds may be for use in a pharmaceutical formulation for treatment of retinal detachment. The compounds may be for use in a pharmaceutical formulation for treatment of diseases of retinal ganglion cells, such as glaucoma. In certain other embodiments, The compounds may be for use in a pharmaceutical formulation for treatment of ocular diseases or conditions, including the following: maculopathies/retinal degeneration, such as: macular degeneration, including age-related macular degeneration (AMD), such as non-exudative age-related macular degeneration and exudative age-related macular degeneration; choroidal neovascularization; retinopathy, including diabetic retinopathy, acute and chronic macular neuroretinopathy, central serous chorioretinopathy; and macular edema, including cystoid macular edema, and diabetic macular edema; uveitis/retinitis/choroiditis, such as acute multifocal placoid pigment epitheliopathy, Behcet's disease, birdshot retinochoroidopachy, infectious (syphilis, Lyme Disease, tuberculosis, toxoplasmosis), uveitis, including intermediate uveitis (pars planitis) and anterior uveitis, multifocal choroiditis, multiple evanescent white dot syndrome (MEWDS), ocular sarcoidosis, posterior scleritis, serpignous choroiditis, subretinal fibrosis, uveitis syndrome, and Vogt-Koyanagi-Harada syndrome; vascular diseases/exudative diseases, such as: retinal arterial occlusive disease, central retinal vein occlusion, disseminated intravascular coagulopathy, branch retinal vein occlusion, hypertensive fundus changes, ocular ischemic syndrome, retinal arterial microaneurysms, Coats disease, parafoveal telangiectasis, hemi-retinal vein occlusion, papillophlebitis, central retinal artery occlusion, branch retinal artery occlusion, carotid artery disease (CAD), frosted branch angitis, sickle cell retinopathy and other hemoglobinopathies, angioid streaks, familial exudative vitreoretinopathy, Eales disease, Traumatic/surgical diseases: sympathetic ophthalmia, uveitic retinal disease, retinal detachment, trauma, laser, PDT, photocoagulation, hypoperfusion during surgery, radiation retinopathy, bone marrow transplant retinopathy; proliferative disorders, such as: proliferative vitreal retinopathy and epiretinal membranes, proliferative diabetic retinopathy. Infectious disorders: ocular histoplasmosis, ocular toxocariasis, ocular histoplasmosis syndrome (OHS), endophthalmitis, toxoplasmosis, retinal diseases associated with HIV infection, choroidal disease associated with HIV infection, uveitic disease associated with HIV Infection, viral retinitis, acute retinal necrosis, proogressive outer retinal necrosis, fungal retinal diseases, ocular syphilis, ocular tuberculosis, diffuse unilateral subacute neuroretinitis, and myiasis; genetic disorders, such as: retinitis pigmentosa, systemic disorders with associated retinal dystrophies, congenital stationary night blindness, cone dystrophies, Stargardt's disease and fundus flavirnaculatus, Best's disease, pattern dystrophy of the retinal pigment epithelium, X-linked retinoschisis, Sorsby's fundus dystrophy, benign concentric maculopathy, Bietti's crystalline dystrophy, pseudoxanthoma elasticum. Retinal tears/holes: retinal detachment, macular hole, giant retinal tear; tumors, such as: retinal disease associated with tumors, congenital hypertrophy of the RPE, posterior uveal melanoma, choroidal hemangioma, choroidal osteoma, choroidal metastasis, combined hamartoma of the retina and retinal pigment epithelium, retinoblastoma, vasoproliferative tumors of the ocular fundus, retinal astrocytoma, intraocular lymphoid tumors; and other diseases and conditions such as: punctate inner choroidopathy, acute posterior multifocal placoid pigment-epitheliopathy, myopic retinal degeneration, acute retinal pigment epithelitis, corneal dystrophies or dysplasias, and the like.

Further embodiments relate to a composition including Compound 1, or a pharmaceutically acceptable salt thereof (e.g., polyacetate salt and triacetate salt), and a pharmaceutical carrier configured for ocular delivery. The composition may be formulated for intraocular, intravitreal, or periocular administration. Compound 1, or a pharmaceutically acceptable salt thereof within the composition protects detached retina photoreceptor cells. Compound 1, or a pharmaceutically acceptable salt thereof within the composition prevents extrinsic-pathway cellular death, including apoptosis in cells of the retinal pigmented epithelium of the eye. Compound 1, or a pharmaceutically acceptable salt thereof within the composition prevents diseases of retinal ganglion cells, such as glaucoma. The composition is sterile, non-pyrogenic and non-toxic to the eye. The composition may further include at least one non-ionic surfactant. The at least one non-ionic surfactant may be Polysorbate 80, Polysorbate 20, Poloxamer, or Tyloxapol, but is not limited to these examples. The at least one non-ionic surfactant may form approximately 0.01%-20% w/w of the composition; alternatively, approximately 0.05%-10% w/w of the composition; and alternatively, approximately 0.1%-3% w/w of the composition. Alternatively, a mixture of non-ionic surfactants may be used, where at least two of the above named, or other non-ionic surfactants, are used together in a ratio, which optimizes the desired pharmacokinetics of the formulation, where the total amounts of the surfactants fall within the above-described limits. The composition may further include an organic cosolvent, such as propylene glycol or dimethylsulfoxide. The organic cosolvent may form approximately 1%-50% w/w of the composition; alternatively, approximately 1%-20% w/w of the composition; and alternatively, approximately 1%-5% w/w of the composition. An isotonicity agent, such as trehalose or mannitol or sorbitol, or a soluble inorganic salt, such as NaCl, may also be added to bring the tonicity of the solution into the 250-400 mOsm/L range. The composition may have a pH in the 2.5-6.0 range, and be buffered by means known to one of skill in the art.

Another embodiment relates to a method of treating an ocular condition, disease, or condition or disease affecting ocular health, comprising administering the composition including Compound 1, or a pharmaceutically acceptable salt thereof, and a pharmaceutical carrier configured for optical delivery to a subject suffering from the ocular condition, disease, or condition or disease affecting ocular health. The ocular condition, disease, or condition or disease affecting ocular health may be retinal detachment, macular degeneration, age-related macular degeneration, non-exudative age-related macular degeneration, exudative age-related macular degeneration, choroidal neovascularization, retinopathy, diabetic retinopathy, acute and chronic macular neuroretinopathy, central serous chorioretinopathy, macular edema, cystoid macular edema, diabetic macular edema, uveitis/retinitis/choroiditis, multifocal placoid pigment epitheliopathy, Behcet's disease, birdshot retinochoroidopathy, infectious (syphilis, Lyme Disease, tuberculosis, toxoplasmosis), uveitis, intermediate uveitis (pars planitis), anterior uveitis, multifocal choroiditis, multiple evanescent white dot syndrome (MEWDS), ocular sarcoidosis, posterior scleritis, serpignous choroiditis, subretinal fibrosis, uveitis syndrome, Vogt-Koyanagi-Harada syndrome; retinal arterial occlusive disease, central retinal vein occlusion, disseminated intravascular coagulopathy, branch retinal vein occlusion, hypertensive fundus changes, ocular ischemic syndrome, retinal arterial microaneurysms, Coats disease, parafoveal telangiectasis, hemi-retinal vein occlusion, papillophlebitis, central retinal artery occlusion, branch retinal artery occlusion, carotid artery disease (CAD), frosted branch angitis, sickle cell retinopathy and other hemoglobinopathies, angioid streaks, familial exudative vitreoretinopathy, Eales disease, sympathetic ophthalmia, uveitic retinal disease, retinal detachment, trauma, laser, PDT, photocoagulation, hypoperfusion during surgery, radiation retinopathy, bone marrow transplant retinopathy, proliferative vitreal retinopathy and epiretinal membranes, proliferative diabetic retinopathy, ocular histoplasmosis, ocular toxocariasis, ocular histoplasmosis syndrome (OHS), endophthalmitis, toxoplasmosis, retinal diseases associated with HIV infection, choroidal disease associated with HIV infection, uveitic disease associated with HIV Infection, viral retinitis, acute retinal necrosis, progressive outer retinal necrosis, fungal retinal diseases, ocular syphilis, ocular tuberculosis, diffuse unilateral subacute neuroretinitis, myiasis, retinitis pigmentosa, systemic disorders with associated retinal dystrophies, congenital stationary night blindness, cone dystrophies, Stargardt's disease, fundus flavimaculatus. Best's disease, pattern dystrophy of the retinal pigment epithelium, X-linked retinoschisis, Sorsby's fundus dystrophy, benign concentric maculopathy, Bietti's crystalline dystrophy, pseudoxanthoma elasticum, retinal detachment, macular hole, giant retinal tear, retinal disease associated with tumors, congenital hypertrophy of the RPE, posterior uveal melanoma, choroidal hemangioma, choroidal osteoma, choroidal metastasis, combined hamartoma of the retina and retinal pigment epithelium, retinoblastoma, vasoproliferative tumors of the ocular fundus, retinal astrocytoma, intraocular lymphoid tumors, punctate inner choroidopathy, acute posterior multifocal placoid pigmentepitheliopathy, myopic retinal degeneration, abnormal retinal pigment epithelium homeostasis, acute retinal pigment epithelitis, glaucoma, corneal dystrophies or dysplasias, and the like. The composition may be administered in an amount sufficient to attenuate cell death within the subject. The composition is administered in an amount sufficient to enhance photoreceptor survival within said subject. The composition is administered in an amount sufficient to protect retinal pigmented epithelium cells within said subject. The composition is administered in an amount sufficient to protect retinal ganglion cells within said subject.

Another embodiment relates to a method of preventing photoreceptor, RPE or retinal ganglion cell death comprising administering to a subject a composition including Compound 1, or a pharmaceutically acceptable salt thereof, and a sterile, non-pyrogenic pharmaceutical carrier. The photoreceptor, RPE or retinal ganglion cell death is Fas-mediated photoreceptor or RPE cell apoptosis. The subject may be at risk of photoreceptor, RPE or retinal ganglion cell death. The composition may be administered to the subject intraocularly, intravitrealy, or periocularly.

Yet another embodiment relates to a method of increasing photoreceptor, RPE or retinal ganglion cell survival including administering a photoreceptor, RPE or retinal ganglion protective composition comprising Compound 1, or a pharmaceutically acceptable salt thereof. The increasing photoreceptor, RPE or retinal ganglion cell survival comprises inhibiting photoreceptor, RPE or retinal ganglion cell apoptosis. The photoreceptor, RPE or retinal ganglion cell death comprises Fas-mediated photoreceptor, RPE or retinal ganglion cell apoptosis. The photoreceptor, RPE or retinal ganglion cell death comprises TRAIL-mediated photoreceptor, RPE or retinal ganglion cell apoptosis. The photoreceptor, RPE or retinal ganglion cell death comprises TNFR-mediated photoreceptor, RPE or retinal ganglion cell necroptosis. The photoreceptor, RPE or retinal ganglion cell death comprises extrinsic pathway-mediated photoreceptor, RPE or retinal ganglion cell pyroptosis. The composition may be administered to the subject systemically via intravenous, subcutaneous or intramuscular injection, or orally, or locally, i.e., intraocularly, intravitrealy, topically, suprachoroidally, subconjunctivally, subretinally or periocularly.

DETAILED DESCRIPTION

Figure 1:
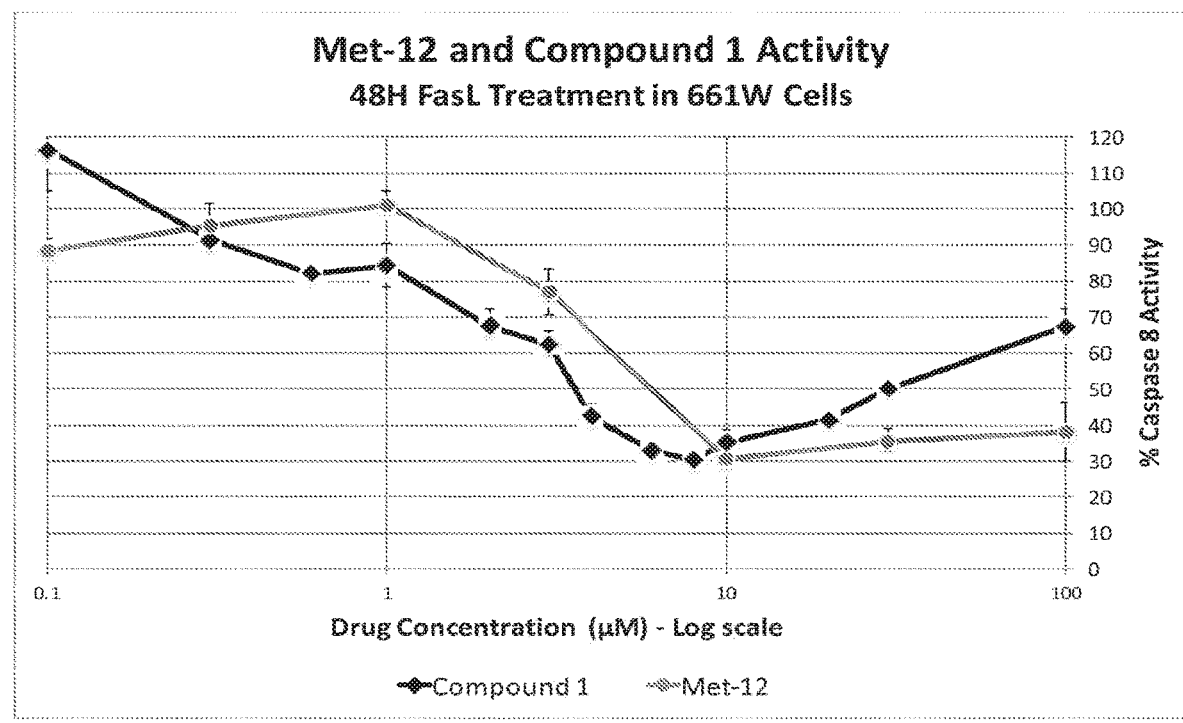
FIG. 1 shows a graph depicting blockade of Fas-induced caspase 8 activation by Met12 and Compound 1 trihydrochloride in 661W cells. 661W cells were, pre-treated with various amounts of either Met-12 or Compound 1 dissolved in DMSO, both at 20 mg/mL for 1 hr Then FasL (500 ng/mL) was added, and Caspase 8 activity was measured at 48 hours after treatment with FasL.

All patents, patent applications and publications, and other literature references cited herein are hereby incorporated by reference in their entirety. The disclosures of these publications in their entireties are hereby incorporated by reference into this application in order to more fully describe the state of the art as known to those skilled therein as of the date of the invention described and claimed herein.

Biologically active peptide compositions, pharmaceutical preparations of biologically active peptide compositions, and methods of using the peptide compositions are described.

The term "therapeutically effective amount" means an amount of a drug or agent (e.g., Compound 1) effective to facilitate a desired therapeutic effect in a particular class of subject (e.g., infant, child, adolescent, adult). As used herein, the term "subtherapeutic" refers to an amount of a pharmaceutical drug or agent that is insufficient to achieve the desired and/or anticipated therapeutic result/outcome upon administration to an average and/or typical subject (e.g., average size, taking no contraindicated pharmaceutical agents, having a similar reaction to the dose as a majority of the population, etc.). U.S. Food and Drug Administration (FDA) recommended dosages are indicative of a therapeutic dose.

As used herein, the terms "pharmaceutical drug" or "pharmaceutical agent" refer to a compound, peptide, macromolecule, or other entity that is administered (e.g., within the context of a pharmaceutical composition) to a subject to elicit a desired biological response. A pharmaceutical agent may be a "drug" or any other material (e.g., peptide, polypeptide), which is biologically active in a human being or other mammal, locally and/or systemically. Examples of drugs are disclosed in the Merck Index and the Physicians Desk Reference, the entire disclosures of which are incorporated by reference herein for all purposes.

As used herein, the term "pharmaceutical formulation" refers to at least one pharmaceutical agent (e.g., Compound 1) in combination with one or more additional components that assist in rendering the pharmaceutical agent(s) suitable for achieving the desired effect upon administration to a subject. The pharmaceutical formulation may include one or more additives, for example pharmaceutically acceptable excipients, carriers, penetration enhancers, coatings, stabilizers, buffers, acids, bases, or other materials physically associated with the pharmaceutical agent to enhance the administration, release (e.g., timing of release), deliverability, bioavailability, effectiveness, etc. of the dosage form. The formulation may be, for example, a liquid, a suspension, a solid, a nanoparticle, emulsion, micelle, ointment, gel, emulsion, coating, etc. A pharmaceutical formulation may contain a single pharmaceutical agent (e.g., Compound 1) or multiple pharmaceutical agents. A pharmaceutical composition may contain a single pharmaceutical formulation or multiple pharmaceutical formulations. In some embodiments, a pharmaceutical agent (e.g., Compound 1) is formulated for a particular mode of administration (e.g., ocular administration (e.g., intravitreal administration, etc.), etc.). A pharmaceutical formulation is sterile, non-pyrogenic and non-toxic to the eye.

As used herein, the term "pharmaceutical composition" refers to the combination of one or more pharmaceutical agents with one or more carriers, inert or active, making the composition especially suitable for diagnostic or therapeutic use in vitro, in vivo or ex vivo. A pharmaceutical composition comprises the physical entity that is administered to a subject, and may take the form of a solid, semi-solid or liquid dosage form, such as tablet, capsule, orally-disintegrating tablet, pill, powder, suppository, solution, elixir, syrup, suspension, cream, lozenge, paste, spray, etc. A pharmaceutical composition may comprise a single pharmaceutical formulation (e.g., extended release, immediate release, delayed release, nanoparticulate, etc.) or multiple formulations (e.g., immediate release and delayed release, nanoparticulate and non-nanoparticulate, etc.). The terms "pharmaceutical composition" and "pharmaceutical formulation" may be used interchangeably.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants see, e.g., Martin, Remington's Pharmaceutical Sciences, 15th Ed., Mack Publ. Co., Easton, Pa. [1975]; herein incorporated by reference in its entirety.

As used herein, the term "pharmaceutically acceptable salt" refers to any acid or base of a pharmaceutical agent or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

As used herein, the term "administration" refers to the act of giving a drug, prodrug, or other agent, or therapeutic treatment (e.g., compositions of the present invention) to a subject (e.g., a subject or in vivo, in vitro, or ex viva cells, tissues, and organs) Exemplary routes of administration to the human body can be through the eyes (ophthalmic), mouth (oral), skin (transdermal), nose (nasal), lungs (inhalant), oral mucosa (buccal), ear, rectal, by injection (e.g., intravenously, subcutaneously, intratumorally, intraperitoneally, etc.) and the like.

As used herein, the term "co-administration" refers to the administration of at least two agent(s) (e.g., Compound 1 and one or more additional therapeutics) or therapies to a subject. In some embodiments, the co-administration of two or more agents/therapies is concurrent. In other embodiments, the co-administration of two or more agents/therapies is sequential (e.g., a first agent/therapy is administered prior to a second agent/therapy). In some embodiments, the two or more therapies are administered concurrently, but released (e.g., absorbed, become bioavailable, etc.) sequentially. Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone.

Provided herein are pharmaceutical preparations of biologically active, aqueous formulations of a photoreceptor-protective peptide, pharmaceutical preparations thereof, and methods of preventing photoreceptor death therewith as well as therapeutic methods.

model of photoreceptor toxicity, in 661W cells, Compound 1 is 10-fold more potent at preventing Caspase 8 activation than Met-12 by $IC_{50}$, and approximately 3-fold more potent than Met-12 measured by dose potency at maximal inhibition. In an in vivo rat model of retinal detachment, Compound 1 is at least 10-fold more potent than is Met-12 at protecting photoreceptor cells from apoptosis, and, unlike Met-12 can be delivered efficaciously in clinically acceptable formulations.

As demonstrated in the examples, Fas inhibition by Compound 1 resulted in significant preservation of photoreceptor cells in viva. In 661W cells, Compound 1 treatment resulted in profound inhibition of the caspase 8 activation. As such, it is believed that administration of Compound 1 to a subject with an ocular condition, disease, or condition or disease affecting ocular health may yield improved protection of retinal cells including, but not limited to, photoreceptors, retinal pigment epithelium cells and retinal ganglion cells, from Fas-mediated apoptosis, resulting in improvement and/or treatment of the ocular condition, disease, or condition or disease affecting ocular health.

In clinical practice, patients generally present with a detachment having already occurred. The animal models of retina-RPE separation show that Fas-pathway activation takes place early and remains elevated throughout the duration of the detachment (Lacks et al. Arch Ophthalmol 2007; 125:1389-1395, Lacks et al. IOVS 2004; 45(12):4563-4569.8). The separation of retina and RPE is also encountered in a broad spectrum of retinal diseases. It is contemplated that the clinical relevance of anti-Fas therapy in retinal cell survival is not limited to retinal detachment. For example, Fas-mediated apoptosis may play a role in photoreceptor cell death in age-related macular degeneration (AMD) (Dunaief et al. Arch Ophthalmol. 2002; 120(11): 1435-1442; Zacks et al. Arch Ophthalmol 2007; Pecrukhin K. New therapeutic targets in atrophic age-related macular degeneration. *Expert Opin Ther Targets*. 2007. 11:625-639; Miller J W. Treatment of age-related macular degeneration: beyond VEGF. *Jpn J Ophthalmol*. 2010. 54:523 528; Rogala J, Zangerl B, Assaad N, Fletcher E L, Kalloniatis M, Formual I

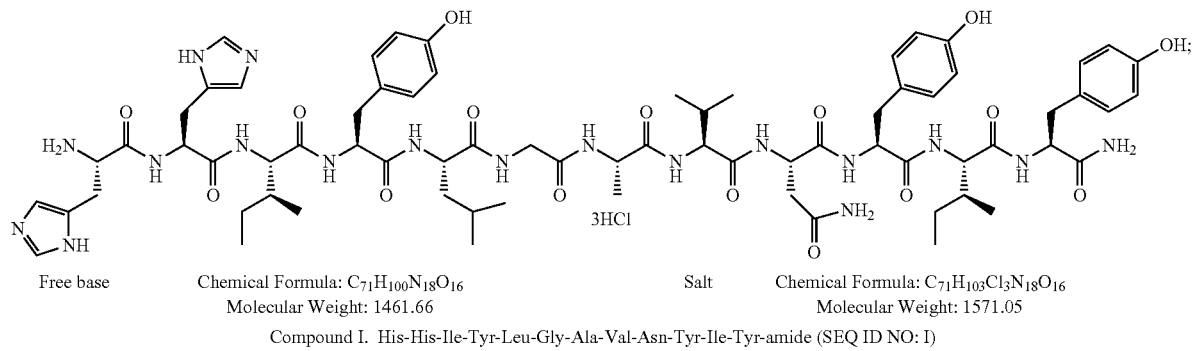 [SMILES: CC[C@H](C)[C@H](NC(=O)[C@H](Cc1ccc(O)cc1)NC(=O)[C@H](CC(N)=O)NC(=O)[C@@H](NC(=O)[C@H](C)NC(=O)CNC(=O)[C@H](CC(C)C)NC(=O)[C@H](Cc1ccc(O)cc1)NC(=O)[C@@H](NC(=O)[C@H](Cc1cnc[nH]1)NC(=O)[C@@H](N)Cc1cnc[nH]1)[C@@H](C)CC)C(C)C)C(=O)N[C@@H](Cc1ccc(O)cc1)C(N)=O]

Free base    Chemical Formula: $C_{71}H_{100}N_{18}O_{16}$            Salt    Chemical Formula: $C_{71}H_{103}Cl_3N_{18}O_{16}$
           Molecular Weight: 1461.66                                   Molecular Weight: 1571.05

Compound I. His-His-Ile-Tyr-Leu-Gly-Ala-Val-Asn-Tyr-Ile-Tyr-amide (SEQ ID NO: I)

Some embodiments relate to a C-terminal amide peptide, Compound 1 (above or a pharmaceutically acceptable salt thereof. Certain embodiments relate to a polyacetate salt of the Compound 1. Certain further embodiments relate to a triacetate salt of the Compound 1.

The compounds may be for use in a pharmaceutical formulation for preventing Fas- or TRAIL mediated apoptosis in the photoreceptors of the eye. In a FasL-induced Nivison-Smith L. In Vivo Quantification of Retinal Changes Associated with Drusen in Age-Related Macular Degeneration. *Invest Ophthalmol Vis Sci*. 2015. 56:1689-1700, herein incorporated by reference in its entirety). Age-related macular degeneration is characterized by progressive degeneration of the RPE and causes outer retinal degeneration and re-organization similar to that which occurs after retinal detachment (Jager et al. N Engl J Med. 2008; 358:2606-17, Johnson et al. Invest Ophthalmol Vis Sci. 2003; 44:4481-488, herein incorporated by reference in their entireties). In the neovascular form of AMD there is also the exudation of fluid under the retina, creating an actual separation of this tissue from the underlying RPE (Jager et al. N Engl J Med. 2008; 358:2606-17, herein incorporated by reference in its entirety). Neovascular AMD can result in prolonged periods of retina-RPE separation and Fas-pathway activation. The utility of anti-Fas treatment would most likely be as an adjunct aimed at protecting retinal cells (such as photoreceptors and retinal pigment epithelium) while the underlying disorder is being treated (Brown et al, N Engl J Med. 2006 Oct. 5; 355(14):1432-44, herein incorporated by reference in its entirety).

Glaucoma is a progressive degenerative ocular condition that is characterized by the death of the retinal ganglion cells (RGCs), and previously published research has demonstrated that the RGCs die by apoptosis (Ji et al. Vision Res. 2005; 45(2): 169-179). Intraocular pressure (IOP) is a major risk factor for glaucoma development and substantial efforts have been devoted to reducing IOP using prostaglandin analogs in order to prevent RGC apoptosis (Doucette and Walter. Ophthalmic Genet. 2016; 12:1-9). Fas has also been implicated in RGC death (Gregory et al. PLoS One. 2011; 6(3):e17659), and animal models of IOP exhibit increased Fas and FasL expression (Ju et al. Brain Res. 2006; 1122(1): 209-221), indicating the potential utility of Fas inhibition as a means to protect RGC viability and mitigate the degenerative nature of glaucoma.

In some embodiments, the described polypeptide can be prepared by methods known to those of ordinary skill in the art. For example, the claimed Compound 1 can be synthesized using standard solid phase polypeptide synthesis techniques (e.g., Fmoc). Alternatively, the polypeptide can be synthesized using recombinant DNA technology (e.g., using bacterial or eukaryotic expression systems), which overexpress both the peptide and an appropriate amidase enzyme to carry out the C-terminal amidation.

Specifically, as described in Example 1, Compound 1 can be obtained by building the Met-12 peptide sequence, $H^{60}HIYLGAINYIY^{71}$ (SEQ ID NO: 2) onto an amino resin, as is known to those of skill in the art to produce after deprotection and resin cleavage its C-terminal amide $H^{60}HIYLGATNYIY^{71}-NH_2$, Compound 1 (SEQ ID NO: 1). Specifically, Compound 1 can be obtained conceptually from the c-Met sequence by a normal amide hydrolysis between residues 59 and 60, and an unnatural breaking of the peptide chain between the peptide nitrogen and the α-carbon of residue 72, rather than at the carbonyl carbon of residue 71. This is not a cleavage, which occurs naturally. Met-12 has been previously described in U.S. Pat. No. 8,343,931, which is incorporated herein in its entirety.

The use of a C-terminally amidated peptide, i.e., Compound 1, was based on a belief that this specific modification might raise the pH at which the peptide is soluble in water or miscible in micelles by removal of the free carboxylic acid, which is significantly deprotonated above pH 3. The resulting species would not have a C-terminal anion at any physiologically relevant pH, or be a zwitterion under any physically relevant circumstances, and would be a tricationic species below about pH 5. This alteration could be mast readily achieved by conversion into an amide or ester, neither of which is deprotonatable under physiological conditions. Amides are more biologically and chemically stable than esters, and also less hydrophobic, so the simple primary amide was chosen.

In certain embodiments, Compound 1 can be produced by converting Met-12 into its C-terminal primary amide, to form Compound 1, although it is generally more practical to build up the peptide from an already aminated first amino acid residue, by use of an amino resin, familiar to one of skill in the art. As noted in the examples section below, Compound 1 was obtained and tested originally as a trihydrochloride, although later a triacetate salt was deemed more advantageous for formulation.

There are certain advantages of using Compound 1 over Met-12. Specifically, as shown in the examples below, Compound 1 can be formulated with surfactants to produce micellar solutions at pHs and additive amounts, which are precedented in ocular formulations. Second, based on the in vitro efficacy assay, Compound 1 is surprisingly 10-fold more potent than Met-12 by $IC_{50}$ determination and approximately 3-fold more potent measured by concentration of maximal inhibition. Specifically, when Met-12 and Compound 1 are tested in the same formulation in vitro, Compound 1 has greater dose potency than Met-12. This allows for the same physiological effect to be achieved with lower amounts of Compound 1 than of Met-12. Third, in in vivo testing in a rat model of retinal detachment, Compound 1 surprisingly is at least five times as potent as Met-12 in preventing apoptosis in photoreceptor cells in the detached portion of the retina. Fourth, in some of the disclosed formulations of Compound 1, efficacy in the rat retinal detachment model is achieved at levels more than 10-fold lower than seen with Met-12. Finally, Compound 1 shows very extended half lives in both vitreous humor, and retinas of rabbits treated intravitreally, and these half lives can be extended to different extents by using different formulations, allowing the overall retinal exposure to Compound 1 to be controlled by the formulation chosen.

In some embodiments, Compound 1 is effective in one or more of: preventing/inhibiting/reducing Fas-mediated photoreceptor apoptosis, preventing apoptosis in cells of the retinal pigmented epithelium of the eye, increasing photoreceptor survival, preventing cell death related to age-related macular degeneration (AMD), preventing cell death related to retinal detachment, etc. In some additional embodiments, Compound 1 is effective in protecting retinal ganglion cells, which receive visual information from photoreceptors via two intermediate neuron types: bipolar cells and retina amacrine cells.

In some embodiments, a therapeutically active amount of Compound 1 or preparation thereof (i.e., a formulation or a composition) is administered to a mammalian subject in need of treatment (e.g., for a particular ocular condition) and at a location sufficient to inhibit or attenuate apoptosis within the patient (e.g., within desired tissue). The preferred subject is a human with an ocular condition, disease, or condition or disease affecting ocular health.

The amount administered is sufficient to yield improved protection of retinal cells and/or retinal ganglion cells, including, but not limited to, photoreceptors, retinal pigment epithelium and retinal ganglia, from Fas-mediated apoptosis, or prevent retinal cell death, resulting in improvement and/or treatment of the ocular condition, disease, or condition or disease affecting ocular health.

The determination of a therapeutically effective dose is within the capability of practitioners in this art. In some embodiments, an effective human dose will be in the range of 5-10,000 µg/eye, 50-5,000 µg/eye, or 100-2.000 µg/eye. Repeated doses are contemplated in order to maintain an effective level (e.g., weekly, every other week, monthly, quarterly, semi-annually etc.).

In some embodiments, a pharmaceutical formulation is a sterile, non-pyrogenic liquid and comprises at least 0.1 mg/ml (e.g., >0.1, >0.2, >0.5, >0.6, >0.7, >0.8, and >0.9), at least 1 mg/ml (e.g., >1 mg/ml, >2 mg/ml, >5 mg/ml, >10 mg/ml, etc.) of a peptide/polypeptide described herein (e.g., 1 mg/ml, 2 mg/ml, 5 mg/ml, 10 mg/ml, or more) of a peptide/polypeptide (e.g., Compound 1).

In some embodiments, a therapeutic dose comprises at least 0.01 ml (e.g., 0.01 ml . . . 0.02 ml . . . 0.05 ml . . . 0.1 ml . . . 0.2 ml . . . 0.5 ml . . . 1 ml . . . 2 ml . . . 3 ml . . . 4 ml, and volumes and ranges therein) of a liquid pharmaceutical formulation comprising a photoreceptor- or RPE-protective peptide/polypeptide (e.g., Compound 1). In some embodiments, a liquid volume of 10 to 500 µl is injected into the human eye (e.g., 10 µl, 20 µl, 30 µl, 40 µl, 50 µl, 75 µl, 100 µl, 200 µl, 300 µl, 400 µl, 500 µl, and volumes and ranges therein). In some embodiments, a volume of 50 to 600 µl is injected into the human eye (e.g., 50 µl, 75 µl, 100 µl, 200 µl, 300 µl, 400 µl, 500 µl, 600 µl, and volumes and ranges therein). In some embodiments, when injected intraoperatively milliliter scale volumes may be used (e.g., up to the total volume of the vitreous cavity (e.g., about 4 ml). In some embodiments the compound may be incorporated into perfusate solution used for maintaining internal ocular pressure during a vitrectomy.

In some embodiments, a single dose is provided (e.g., to treat an acute condition (e.g., retinal detachment). In some embodiments, multiple doses (e.g., daily, weekly, monthly, etc.) are provided for treatment of a chronic condition. The formulation may be different depending on the needed duration of exposure for the condition being treated.

In some embodiments, treatment dosages are titrated upward from a low level to optimize safety and efficacy. In some embodiments for intravitreal injection, a dose includes 0.01 to 5 mg of peptide (e.g., 0.1 and 2.0 mg).

In some embodiments, pharmaceutical preparations (i.e., formulations and/or compositions) comprise one or more excipients. Excipients suitable for ocular application, include, but are not limited to, tonicity agents, preservatives, chelating agents, buffering agents, surfactants, cosolvents and antioxidants. Suitable tonicity-adjusting agents include mannitol, sodium chloride, glycerin, sorbitol and the like. Suitable preservatives include p-hydroxybenzoic acid ester, benzalkonium chloride, benzododecinium bromide, polyquaternium-1 and the like. Suitable chelating agents include sodium edetate and the like. Suitable buffering agents include phosphates, borates, citrates, acetates, tromethamine, and the like. Suitable surfactants include ionic and nonionic surfactants, though nonionic surfactants are preferred, such as polysorbates, polyethoxylated castor oil derivatives, polyethoxylated fatty acids, polyethoxylated alcohols, polyoxyethylene-polyoxypropylene block copolymers (Poloxamer), and oxyethylated tertiary octylphenol formaldehyde polymer (Tyloxapol). Other suitable surfactants may also be included. Suitable antioxidants include sulfites, thiosulfate, ascorbates, BHA, BHT, tocopherols, and the like.

The compositions of the present invention optionally comprise an additional active agent. Such additional active agents might include anti-TNF antibodies, such as Adalimumab (Ophthalmic. Surg Lasers Imaging Retina 45, 332 (2014), Curr Eye Res 39, 1106 (2014)) or etanercept (PLoS One, 7, e40065), or kinase inhibitors shown to preserve retinal structure such as the ROCK inhibitor Y-27632 (Molecular Medicine Reports 12, 3655 (2015)), the adenosine kinase inhibitor ABT-702 (Life Sci 93, 78 (2013), or the iNK inhibitory peptide D-JNK-1 (Diabetes 50, 77 (2001), Adv Exptl Med Bial 854, 677 (2016), or docosahexaenoic acid (J Lipid Res, 54.2236 (2013)) or the RXR pan-agonist PA024 (ibid) or necrostatin, or RIP kinase inhibitors such as Dabrafenib. (Cell Death Dis 5, 1278 (2014))

In some exemplary embodiments, at least one of excipients, such as, Polysorbate 20 (e.g., up to 3%), Poloxamer 407 (e.g., up to 2%), Tyloxapol (e.g., up to 3%), cremophor (e.g., up to 1%); and/or cosolvents (e.g., between 0.5 and 50%), such as N,N-Dimethylacetamide, ethanol, PEG-400, propylene glycol, dimethylsulfoxide (DMSO); oils, or cyclodextrins may be added to a pharmaceutical preparation.

In further exemplary embodiments, at least one nonionic surfactant (e.g., 0.1%-20% w/w/ of the composition), such as Polysorbate 80, Polysorbate 20, Poloxamer, or Tyloxapol may be included in the pharmaceutical composition. In addition, an organic cosolvent, such as propylene glycol or dimethylsulfoxide in an amount of approximately 1-50%, may be included in the pharmaceutical composition. Alternatively, an organic cosolvent, such as N,N-Dimethylacetamide, ethanol, PEG-400, propylene glycol, DMSO in an amount of approximately 1-20%, may be included in the pharmaceutical composition. Alternatively, an organic cosolvent, such as propylene glycol or dimethylsulfoxide in an amount of approximately 1-5%, may be included in the pharmaceutical composition. Alternatively, an isotonicity agent such as mannitol, sorbitol, glucose or trehalose, or an inorganic salt such as sodium chloride may be included in the pharmaceutical composition, in amounts needed to bring the tonicity of the composition into the 250-400 mOsm/L range.

The pH of the composition may be in the 2.5-6.0 range. The pH may be controlled by an appropriate buffer and be in the 3.0-5.0 range or 3.5-4.5 range.

In another exemplary embodiment, at least one nonionic surfactant (e.g., 0.5%-10% w/w/ of the composition), such as Polysorbate 80, Polysorbate 20, Poloxamer, or Tyloxapol may be included in the pharmaceutical composition. In addition, an organic cosolvent, such as propylene glycol or dimethylsulfoxide in an amount of approximately 1-50%, may be included in the pharmaceutical composition. Alternatively, an organic cosolvent, such as propylene glycol or dimethylsulfoxide in an amount of approximately 1-20%, may be included in the pharmaceutical composition. Alternatively, an organic cosolvent, such as N,N-Dimethylacetamide, ethanol, PEG-400, propylene glycol, DMSO in an amount of approximately 1-5%, may be included in the pharmaceutical composition. Alternatively, an isotonicity agent such as mannitol, sorbitol, glucose or trehalose, or an inorganic salt such as sodium chloride may be included in the pharmaceutical composition, in amounts needed to bring the tonicity of the composition into the 250-400 mOsm/L range. The pH of the composition may be in the 2.5-6.0 range. The pH may be controlled by an appropriate buffer and be in the 3.0-5.0 range or 3.5-4.5 range.

In yet further exemplary embodiment, at least one nonionic surfactant (e.g., 1%-3% w/w/ of the composition), such as Polysorbate 80, Polysorbate 20, Poloxamer, or Tyloxapol may be included in the pharmaceutical composition. In addition, an organic cosolvent, such as propylene glycol or dimethylsulfoxide in an amount of approximately 1-50%, may be included in the pharmaceutical composition. Alternatively, an organic cosolvent, such as N,N-Dimethylacetamide, ethanol, PEG-400, propylene glycol, DMSO in an amount of approximately 1-20%, may be included in the pharmaceutical composition. Alternatively, an organic cosolvent, such as propylene glycol or dimethylsulfoxide in an amount of approximately 1-5%, may be included in the pharmaceutical composition. Alternatively, an isotonicity agent such as mannitol, sorbitol, glucose or trehalose, or an inorganic salt such as sodium chloride may be included in in the pharmaceutical composition, in amounts needed to bring the tonicity of the composition into the 250-400 mOsm range. The pH of the composition may be in the 2.5-6.0 range. The pH may be controlled by an appropriate buffer and be in the 3.0-5.0 range or 3.5-4.5 range.

In some embodiments, the pharmaceutical composition may include Compound 1 or a pharmaceutically acceptable salt thereof, and Poloxamer 407 (e.g., 0.1-2% w/w/ of the composition) an aqueous medium having pH in the 3.0-6.0 range.

In some embodiments, the pharmaceutical composition may include Compound 1 or a pharmaceutically acceptable salt thereof, and Poloxamer 407 (e.g., 0.1-2% w/w/ of the composition) in an aqueous medium buffered by sodium propanoate/propanoic acid or sodium acetate/acetic acid having a pH in the 4.0-5.0 range.

In some embodiments, the pharmaceutical composition may include Compound 1 or a pharmaceutically acceptable salt thereof, and Poloxamer 407 (e.g., 0.1-2% w/w/ of the composition) in an aqueous medium buffered by sodium propanoate/propanoic acid or sodium acetate/acetic acid having a pH in the 4.0-5.0 range, and made isotonic by 3-5% mannitol.

In some further embodiment, the pharmaceutical composition may include Compound 1, or a pharmaceutically acceptable salt thereof, Polysorbate-20 (e.g., 0.1-3% w/w/ of the composition), and propylene glycol (e.g., 3% w/w/ of the composition) in an aqueous medium in the pH range of 3.0-6.0.

In certain further embodiments, the pharmaceutical composition may include Compound 1, or a pharmaceutically acceptable salt thereof, Polysorbate-20 (e.g., 0.1-3% w/w/ of the composition), and propylene glycol (e.g., 3% w/w/ of the composition) in an aqueous medium buffered by sodium acetate/acetic acid in the pH range of 4.0-5.0.

In some further embodiment, the pharmaceutical composition may include Compound 1, or a pharmaceutically acceptable salt thereof, Polysorbate-20 (e.g., 0.1-3% w/w/ of the composition), and mannitol (e.g., 3-5% w/w/ of the composition) in an aqueous medium in the pH range of 3.0-6.0.

In certain further embodiments, the pharmaceutical composition may include Compound 1, or a pharmaceutically acceptable salt thereof, Polysorbate-20 (e.g., 0.1-3% w/w/ of the composition), and mannitol (e.g., 3-5% w/w/ of the composition) in an aqueous medium buffered by sodium acetate/acetic acid in the pH range of 4.0-5.0.

In some embodiments, the pharmaceutical composition may include Compound 1 or a pharmaceutically acceptable salt thereof, and Poloxamer 407 (e.g., 0.1-2% w/w/ of the composition) and Polysorbate 20 (e.g., 0.1-2% w/w/ of the composition) in an aqueous medium having pH in the 3.0-6.0 range.

In some embodiments, the pharmaceutical composition may include Compound 1 or a pharmaceutically acceptable salt thereof, and Poloxamer 407 (e.g., 0.1-2% w/w/ of the composition) and Polysorbate 20 (e.g., 0.1-2% w/w/ of the composition) in an aqueous medium buffered by sodium propanoate/propanoic acid or sodium acetate/acetic acid having a pH in the 4.0-5.0 range.

In some embodiments, the pharmaceutical composition may include Compound 1 or a pharmaceutically acceptable salt thereof, and Poloxamer 407 (e.g., 0.1-2% w/w/ of the composition) and Polysorbate 20 (e.g., 0.1-2% w/w/ of the composition) in an aqueous medium buffered by sodium propanoate/propanoic acid or sodium acetate/acetic acid having a pH in the 4.0-5.0 range, and made isotonic by 3-5% mannitol.

In some embodiments, the pharmaceutical compositions as described above may include Compound 1, but not chloride as a counterion, with acetate being a preferred alternative. Such compositions may show superior properties to those containing chloride ion.

In some embodiments, the weight ratio of the peptide/polypeptide (e.g., Compound 1) is 1%-25% relative to the weight of the non-aqueous excipients in the pharmaceutical formulation, which is conversely 0.1-20% excipients, such as Poloxamer, Polysorbate 20, propylene glycol and mannitol.

This weight ratio of the peptide/polypeptide (e.g., Compound 1) relative to the weight of the pharmaceutical formulation may be at least about 0.1%, at least 0.5%, at least 1%, at least about 2%, at least about 3%.

The following two exemplary compositions, having an amount of each ingredient in the range indicated, will provide two of several compositions that may be used to treat or prevent various ocular diseases or conditions (e.g., of the retina) or preventing retinal cell death resulting from ocular diseases or conditions or the like in a subject:

Exemplary Formulation I:

| Compound 1 triacetate salt | 0.1-2 mg/mL |
|---|---|
| Poloxamer 407 | 0.01-0.5% |
| Additives (e.g., Mannitol) | 2.5-5% |
| Acetic acid | 10 mM |
| NaOH | To pH >3 |
| Water (WFI) | To 100% |

Exemplary Formulation II:

| Compound 1 triacetate salt | 0.1-2 mg/mL |
|---|---|
| Polysorbate 20 | 0.1-1.0% |
| Additives (e.g., Mannitol) | 2.5-5% |
| Acetic acid | 10 mM |
| NaOH | To pH >3 |
| Water (WFI) | To 100% |

In some embodiments, the compositions of the present invention are administered ocularly, for example, using the techniques described herein, and/or other techniques (e.g. injection, topical administration, etc.) known to those in the art (See, e.g., Janoria et al., *Expert Opin Drug Deliv.*, 4(4): 371-388 (July 2007); Ghate & Edelhauser, *Expert Opin Drug Deliv.*, 3(2):275-87 (2006); Bourges et al., *Adv Drug Deliv Rev.*, 58(11):1182-202 (2006), Epub 2006 Sep. 22; Gomes Dos Santos et al., *Curr Pharm Biotechnol.*, 6(1):7-15 (2005); herein incorporated by reference in their entireties). The composition may be administered using any method known to those of ordinary skill in the art. Non-limiting examples include topical, subconjunctival, sub-Tenon's, intravitreal, subretinal, or injection into the anterior chamber of the eye of a subject. Other modes of administration include systemic administration, including intravenous administration as well as oral administration. In certain embodiments, the composition is administered intravitreally.

Certain embodiments relate to a pharmaceutical composition comprising the Compound 1 polypeptide and a pharmaceutically acceptable carrier. Any carrier which can supply a polypeptide without destroying the vector within the carrier is a suitable carrier, and such carriers are well known in the art.

The composition can be formulated and packaged suitably for parenteral, oral, or topical administration. For example, a parenteral formulation would be a sterile, non-pyrogenic product and could consist of a prompt or sustained release liquid preparation, dry powder, emulsion, suspension, or any other standard formulation. An oral formulation of the pharmaceutical composition could be, for example, a liquid solution, such as an effective amount of the composition dissolved in diluents (e.g., water, saline, juice, etc.), suspensions in an appropriate liquid, or suitable emulsions. An oral formulation could also be delivered in tablet form, and could include excipients, colorants, diluents, buffering agents, moistening agents, preservatives, flavoring agents, and pharmacologically compatible excipients. A topical formulation could include compounds to enhance absorption or penetration of the active ingredient through the skin or other affected areas, such as dimethylsulfoxide and related analogs. The pharmaceutical composition could also be delivered topically using a transdermal device, such as a patch, which could include the composition in a suitable solvent system with an adhesive system, such as an acrylic emulsion, and a polyester patch. Sterile compositions could be delivered via eye drops or other topical eye delivery method. Sterile, nonpyrogenic compositions may be delivered intraocularly, anywhere in the eye including, for example, the vitreous cavity, the anterior chamber, etc. Sterile, non-pyrogenic compositions may be delivered intravitrealy as is commonly done with intravitreal injections of Lucentis (ranabizumab), Avastin (bevacizumab), triamcinolone acetonide, antibiotics, etc. Compositions may be delivered periocularly (e.g. to the tissue around the eyeball (globe) but within the bony orbit). Compositions may be delivered via intraocular implant (e.g. gancyclovir implant, fluocinolone implant, etc.). In intraocular implant delivery, devices containing compositions of the present invention are surgically implanted (e.g. within the vitreous cavity), and the drug is released into the eye (e.g. at a predetermined rate). Compositions may be administered using encapsulated cell technology (e.g. by Neurotech) in which genetically modified cells are engineered to produce and secrete composition comprising the Compound 1 polypeptide. Compositions may be delivered via transcleral drug delivery using a device sutured or placed next to the globe that would slowly elute the drug, which would then diffuse into the eye.

Some embodiments relate to compositions, kits, systems, and/or methods to prevent, inhibit, block, and/or reduce photoreceptor, RPE cell or retinal ganglion cell death. Some embodiments relate to inhibition of apoptosis of photoreceptors. Some embodiments relate to inhibition of apoptosis in cells of the retinal pigmented epithelium of the eye. Some embodiments relate to inhibition of apoptosis in cells of the retinal ganglia of the eye. In some embodiments, photoreceptor death and/or apoptosis and/or retinal pigmented epithelium cell apoptosis and/or apoptosis and/or retinal ganglion cell apoptosis and/or death is caused by retinal detachment, age-related macular degeneration, glaucoma, trauma, cancer, tumor, inflammation, uveitis, diabetes, hereditary retinal degeneration, and/or a disease affecting photoreceptor cells, abnormal retinal pigment epithelium or retinal ganglia.

In some embodiments, the present invention enhances photoreceptor, RPE or retinal ganglion cell viability and/or inhibits photoreceptor death (e.g. during retinal detachment and/or is ocular conditions which do not involve retinal detachment.

In some embodiments, the present invention finds utility in enhanced photoreceptor, RPE or retinal ganglion cell viability and/or inhibits photoreceptor, RPE or retinal ganglion cell death in a variety of conditions and/or diseases including, but not limited to macular degeneration (e.g. dry, wet, non-exudative, or exudative/neovascular), ocular tumors, glaucoma, hereditary retinal degenerations (e.g. retinitis pigmentosa, Stargardt's disease. Usher Syndrome, etc.), ocular inflammatory disease (e.g. uveitis), ocular infection (e.g. bacterial, fungal, viral), autoimmune retinitis (e.g. triggered by infection), trauma, diabetic retinopathy, choroidal neovascularization, retinal ischemia, retinal vascular occlusive disease (e.g. branch retinal vein occlusion, central retinal vein occlusion, branch retinal artery occlusion, central retinal artery occlusion, etc.), pathologic myopia, angioid streaks, macular edema (e.g. of any etiology), central serous chorioretinopathy.

Some embodiments relate to administration of a composition to inhibit photoreceptor, RPE or retinal ganglion cell death (e.g. apoptosis). In some embodiments, a composition comprises a pharmaceutical, small molecule, peptide, nucleic acid, molecular complex, etc. In some embodiments, the present invention provides administration of a photoreceptor, RPE or retinal ganglion cell protective polypeptide to inhibit photoreceptor or RPE or retinal ganglion cell apoptosis.

Some embodiments relate to a method of employing a polypeptide to attenuate the activation of one or more members of the TNFR superfamily, desirably Fas or TRAIL in photoreceptors and/or retinas. In some embodiments, such method is employed, for example, to inhibit cell death (e.g., apoptosis) in cells and tissues, and it can be employed in vivo, ex vivo or in vitro. Thus, Compound 1 may be used for attenuating cell death (e.g. retinal cell death) in accordance with such methods. For in vitro application, the Compound 1 may be provided to cells, typically a population of cells (e.g., within a suitable preparation, such as a buffered solution) in an amount and over a time course sufficient to inhibit apoptosis within the cells or to inhibit inflammation. If desired, a controlled population untreated with the inventive polypeptide can be observed to confirm the effect of the inventive polypeptide in reducing the inhibition of cell death or inflammation within a like population of cells.

In some embodiments, provided herein are methods of treating various ocular diseases or conditions (e.g., of the retina) or preventing retinal cell death from resulting from ocular diseases or conditions, including the following: glaucoma, maculopathies/retinal degeneration, such as: macular degeneration, including age-related macular degeneration (AMD), such as non-exudative age-related macular degeneration and exudative age-related macular degeneration; choroidal neovascularization; retinopathy, including diabetic retinopathy, acute and chronic macular neuroretinopathy, central serous chorioretinopathy; and macular edema, including cystoid macular edema, and diabetic macular edema; uveitis/retinitis/choroiditis, such as acute multifocal placoid pigment epitheliopathy, Behcet's disease, birdshot retinochoroidopathy, infectious (syphilis, Lyme Disease, tuberculosis, toxoplasmosis), uveitis, including intermediate uveitis (pars planitis) and anterior uveitis, multifocal choroiditis, multiple evanescent white dot syndrome (MEWDS), ocular sarcoidosis, posterior scleritis, serpignous choroiditis, subretinal fibrosis, uveitis syndrome, and Vogt-Koyanagi-Harada syndrome; vascular diseases/exudative diseases, such as: retinal arterial occlusive disease, central retinal vein occlusion, disseminated intravascular coagulopathy, branch retinal vein occlusion, hypertensive fundus changes, ocular ischemic syndrome, retinal arterial microaneurysms, Coats disease, parafoveal telangiectasis, hemi-retinal vein occlusion, papillophlebitis, central retinal artery occlusion, branch retinal artery occlusion, carotid artery disease (CAD), frosted branch angitis, sickle cell retinopathy and other hemoglobinopathies, angioid streaks, familial exudative vitreoretinopathy. Eales disease, Traumatic/surgical diseases: sympathetic ophthalmia, uveitic retinal disease, retinal detachment, trauma, laser, PDT, photocoagulation, hypoperfusion during surgery, radiation retinopathy, bone marrow transplant retinopathy; proliferative disorders, such as: proliferative vitreal retinopathy and epiretinal membranes, proliferative diabetic retinopathy. Infectious disorders: ocular histoplasmosis, ocular toxocariasis, ocular histoplasmosis syndrome (OHS), endophthalmitis, toxoplasmosis, retinal diseases associated with HIV infection, choroidal disease associated with HIV infection, uveitic disease associated with HIV Infection, viral retinitis, acute retinal necrosis, progressive outer retinal necrosis, fungal retinal diseases, ocular syphilis, ocular tuberculosis, diffuse unilateral subacute neuroretinitis, and myiasis; genetic disorders, such as: retinitis pigmentosa, systemic disorders with associated retinal dystrophies, congenital stationary night blindness, cone dystrophies, Stargardt's disease and fundus flavimaculatus, Best's disease, pattern dystrophy of the retinal pigment epithelium, X-linked retinoschisis, Sorsby's fundus dystrophy, benign concentric maculopathy, Bietti's crystalline dystrophy, pseudoxanthoma elasticum. Retinal tears/holes: retinal detachment, macular hole, giant retinal tear; tumors, such as: retinal disease associated with tumors, congenital hypertrophy of the RPE, posterior uveal melanoma, choroidal hemangioma, choroidal osteoma, choroidal metastasis, combined hamartoma of the retina and retinal pigment epithelium, retinoblastoma, vasoproliferative tumors of the ocular fundus, retinal astrocytoma, intraocular lymphoid tumors; and other diseases and conditions such as: punctate inner choroidopathy, acute posterior multifocal placoid pigmentepitheliopathy, myopic retinal degeneration, acute retinal pigment epithelitis corneal dystrophies or dysplasias and the like.

Certain embodiments provide methods for increasing photoreceptor, RPE or retinal ganglion survival comprising administering a pharmaceutical composition comprising Compound 1, or a pharmaceutically acceptable salt thereof. The pharmaceutical compound may be administered in the form of a composition which is formulated with a pharmaceutically acceptable carrier and optional excipients, adjuvants, etc. in accordance with good pharmaceutical practice. The composition may be in the form of a solid, semi-solid or liquid dosage form: such as powder, solution, elixir, syrup, suspension, cream, drops, paste and spray. As those skilled in the art would recognize, depending on the chosen route of administration (e.g. eye drops, injection, etc.), the composition form is determined. In general, it is preferred to use a sterile, unit dosage form of the inventive inhibitor in order to achieve an easy and accurate administration of the active pharmaceutical compound. In general, the therapeutically effective pharmaceutical compound is present in such a dosage form at a concentration level ranging from about 0.01% to about 1.0% by weight of the total composition: i.e., in an amount sufficient to provide the desired unit dose.

In some embodiments, the pharmaceutical composition may be administered in single or multiple doses. The particular route of administration, product requirements and the dosage regimen will be determined by one of skill in keeping with the condition of the individual to be treated and said individual's response to the treatment. In some embodiments, the composition in a unit dosage form for administration to a subject, comprising a pharmaceutical compound and one or more nontoxic pharmaceutically acceptable carriers, adjuvants or vehicles. The amount of the active ingredient that may be combined with such materials to produce a single dosage form will vary depending upon various factors, as indicated above. A variety of materials can be used as carriers, adjuvants and vehicles in the composition of the invention, as available in the pharmaceutical art. Injectable preparations, such as oleaginous solutions, suspensions or emulsions, may be formulated as known in the art, using suitable dispersing or wetting agents and suspending agents, as needed. The sterile injectable preparation may employ a nontoxic parenterally acceptable diluent or solvent such as sterile nonpyrogenic water or 1,3-butanediol. Among the other acceptable vehicles and solvents that may be employed are 5% dextrose injection, Ringer's injection and isotonic sodium chloride injection (as described in the USP/NF). In addition, sterile, fixed oils may be conventionally employed as solvents or suspending media. For this purpose, any bland fixed oil may be used, including synthetic mono-, di- or triglycerides. Fatty acids such as oleic acid can also be used in the preparation of injectable compositions.

There are several possible routes of drug delivery into the ocular tissues. The route of administration depends on the target tissue. In certain embodiments, the routes of administration may be conventional routes of administrations, such as either topical or systemic. Topical administration, mostly in the form of eye drops may be employed to treat disorders affecting the anterior segment of the eye. Administration may also be via direct injection, e.g., intravitreal injection, which involves injection of a drug solution directly into the vitreous humor (VH) using, e.g., 30 G needle. Other routes of administration, e.g., using drug carriers may also be suitable.

In some embodiments, the composition may be administered ocularly (i.e., to the eye), for example, using the techniques described herein, and/or other techniques (e.g. injection, topical administration, etc.) known to those in the art (See, e.g., Janoria et al. Expert Opinion on Drug Delivery. July 2007, Vol. 4, No. 4, Pages 371-388; Ghate & Edelhauser. Expert Opin Drug Deliv. 2006 March; 3(2): 275-87; Bourges et al. Adv Drug Deliv Rev. 2006 Nov. 15; 58(10:1182-202. Epub 2006 Sep. 22; Games Dos Santos et al. Curr Pharm Biotechnol. 2005 February; 6(1):7-15; herein incorporated by reference in their entireties.

In some embodiments, the composition may be co-administered with one or more other agents for effective protection of photoreceptors and/or inhibition of apoptosis.

In some embodiments, kits are provided comprising Compound 1, or pharmaceutical preparations thereof. In some embodiments, kits further provide devices, materials, buffers, controls, instructions, containers (e.g., vials, syringes), etc. (e.g., for administration). For example, any of the above mentioned compositions and/or formulations may be packaged. Any of the above mentioned compositions and formulations may be distributed in prefilled syringes. The composition and processing result in a sterile, non-pyrogenic product. The package functions to maintain the sterility of the product.

EXAMPLES

Experiments were conducted during development of the described embodiments to develop a biologically active pharmaceutical formulation of Compound 1 (e.g., for intravitreal administration). The photoreceptor protective properties of Compound 1 were examined in vitro and in vivo following dosing of peptide solutions in DMSO. Compound 1 has poor aqueous solubility above pH-3 and high tendency to form gels or precipitates in aqueous environments. From the proportional adjustment of efficacious dose in rats to human according to the intra species vitreous volume a target concentration of 10-20 mg/mL was defined as an initial goal, with lower concentrations (0.5-2.0 mg/mL) becoming more desirable as testing demonstrated the surprisingly superior potency and exposure of the described embodiments. (Examples 1-6).

Example 1: Compound 1 Preparation and Testing

The Compound 1 peptide (Peptide His-His-Ile-Tyr-Leu-Gly-Ala-Val-Asn-Tyr-e-Tyr-NH$_2$; SEQ ID NO: 1) was synthesized on Fmoc-Amide-AMS resin via Fmoc chemistry, by multiple suppliers. Fmoc protected amino acids were purchased from GL Biochem. Reagents for coupling and cleavage were purchased from Aldrich. Solvents were purchased from Fisher Scientific.

The peptide chain was assembled on resin by repetitive removal of the Fmoc protecting group and coupling of protected amino acid. DIC and HOBt were used as coupling reagent, and NMM was used as base; 20% piperidine in DMF was used as de-Fmoc-reagent. Ninhydrin test was performed after each coupling to check the coupling efficiency.

After the last coupling, resin was washed and dried, and peptide was cleaved off resin by treating with cleavage cocktail (TFA/Tis/H$_2$O/DOTA: 95/3/2/2). Peptide was precipitated from cold ether and collected by filtration, 13 g of crude with purity 46% was obtained (yield: 127%).

For each of two preparative purification runs, around 4.4 g of crude peptide was purified by 2-inch polymer column with TFA buffer (buffer A, 0.1% TEA in water; buffer B, 100% acetonitrile), resultant fractions with purity >85% were further purified by 2-inch C18 column with TFA buffer. Collected fractions with purity >95% were lyophilized to dry, and 3.68 g of material as TFA salt with purity >95% was obtained from 8.8 g of crude. To the 1.5 g of peptide (TFA as counter ion), enough HCl aqueous solution was added to dissolve the peptide. Peptide in HCl aqueous solution was lyophilized to dry. 1.4 g final peptide as HCl salt was obtained with purity 97.0%. HPLC 15% ACN in water 0.1% TFA, Venusil XBP-C18 4.6×250 mm 1.0 mL/min; RT 17.79 min. Mass spectrum APCI MH$^+$ 1461.5.

Microanalysis. Found; C, 52.21; H, 6.49; N, 15.42; CI, 6.73. KF, 3.75%. Calculated for $C_{71}H_{100}N_{18}O_{16}$.3HCl.3.4H$_2$O: C, 52.24; H, 639; N, 15.45; Cl, 6.52. KF, 3.75%. % Active=89.55%.

Later samples of the peptide were still synthesized as the trifluoroacetate salt, but an anion exchange was carried out with acetate, to give Compound 1 as its triacetate salt.

Example 2: Compound 1 pH-Solubility Profile

Compound 1 obtained as a trihydrochloride salt, as described in Example 1, and was screened for aqueous solubility at different pHs, by carrying out pH titrations according to the following protocol. In some cases Met-12 was run through an identical experimental procedure to determine its solubility pH profile under the same conditions. Multiple previous experiments had failed to find any conditions where Met-12 could be formulated satisfactorily in a largely aqueous medium at any pH above 2.7.

Compound 1 (10 nag) was dissolved in water (270-900 µL) in a 2 mL clear plastic centrifuge tube with vortexing to give a pH~2.4 solution. In all cases the peptide formed a clear solution suggesting at low pH a solubility of at least 40 mg/mL. This solution was then diluted with the appropriate amount of cosolvent or other excipient (sugar, surfactant etc.) to produce a clear acidic solution of 10 mg of Compound 1 in 900 µL of the test solution at room temperature (22-23° C.). Small aliquots of a basic solution (usually sodium hydroxide 1.0 M or 0.1 M, but sometimes other bases when investigating buffers) were added using a microliter syringe. Between additions the solution was mixed by vortexing, and the solution was inspected visually for precipitates of various types, turbidity, as a likely sign of microprecipitates, and viscosity to detect gel formation. pH measurements were taken at all these observation points. Some experiments titrated from the endogenous low pH to pH 10, but later titrations were not carried much above pH 7, or sometimes even lower.

Titration of the aqueous Compound 1 solution with sodium hydroxide suggested a slightly better pH-limited solubility than Met-12, with a clear mobile solution to about pH 3.3, as opposed to pH 3.0 for Met-12. However, when titrations were carried out using five buffering bases, Tris, histidine, sodium citrate, sodium borate and sodium phosphate, in place of sodium hydroxide viscosity and signs of aggregation were generally seen in the pH 2.6-2.9 range. Fibril formation was also seen below pH 3 in one or two cases. From these experiments it appears that Compound 1 has no better an aqueous solubility-pH profile than Met-12.

Example 3: pH-Dependent Solubility of Compound 1 in Cosolvent Mixtures

The pH-dependent solubility of Compound 1 was examined using cosolvents and additives and compared with Met-12 solubility under the same conditions.

The 70% DMSO experiment was similar to the Met-12 titration with a gel forming around pH 5.5, but in this case, probably because of the inability of the C-terminus to ionize, the gel did not re-dissolve at higher pHs.

70% Propylene glycol (PG) improved the solubility of Compound 1 as compared to Met-12, with no gelling occurring until around pH 4.7, as compared to pH 3.2 for Met-12, and then remaining a gel to pH 10. This titration was repeated with lower amounts of PG (35%, 10%), but neither appeared to improve the solubility profile over water alone, 70% PEG400 and 70% glycerol solutions did not appear to be useful, and neither did the two sugar additives, 10% mannitol or 10% trehalose.

From these experiments it was concluded that propylene glycol may be a useful cosolvent under some limiting circumstances for Compound 1, but not for Met-12.

Example 4: pH-dependent Solubility of Compound 1 in Non-Ionic Surfactant Mixtures Surprisingly, some of the surfactants examined provided significant improvements in the pH-solubility profile of Compound 1 whereas none of the surfactants tested improved the pH-solubility profile of Met-12. Compound 1 in the presence of 10% Tyloxapol remained clear, and of acceptable viscosity, until the pH was above 5.87. With 10% Polysorbate 80, the clear solution did not become appreciably viscous until above pH 6.36. With 10% Polysorbate 20, fibrils were observed at pH 3.2 but with no signs of turbidity or gelling until pH 7.14. The 10% Poloxamer 407 was somewhat ambiguous as to where the onset of insolubility might occur, as a second phase was clearly present in the pH 5-9 range, although the solution appeared to be mobile. This appeared to consist of very large clear globules formed in the solution. This is believed to be an artifact of the high Poloxamer concentration, as 15% Poloxamer solutions gel completely at 27° C., whereas 10% Poloxamer does not gel appreciably at 25° C., but various additives can either raise or lower the sol-gel critical temperature, and the usual viscosity measurements for gelling will not pick up the initial appearance of a separate gel phase efficiently. Therefore, it is believed that there was no loss of solubility of the peptide in the mixture, but the high amount of Poloxamer was forming two Poloxamer phases, a sol phase, and a gel phase. Povidone K30 produced a viscous solution at pH 3.60, which gelled above pH 4.0.

Some of the surfactants were then titrated down with respect to the amount of surfactant added. When Polysorbate 20 was titrated down to 3% and 1% concentrations, fibril formation was seen below pH 2.5, but in both cases other signs of precipitation were not seen until pH 4.14 and 3.76 respectively. Poloxamer 407 at 4% produced a small and apparently not increasing, numbers of fibrils at the initiation of the titration, but no other signs of precipitation until above pH 6.2, and at 2% produced a clear solution until above pH 5.6. At 0.5% fibrils were seen in solution once the titration was begun, but no further signs of precipitation were seen until above pH 4.5.

Compound 1 was clearly superior to Met-12 in most of the surfactants examined, notably Polysorbate 80, Poloxamer 407 and Tyloxapol, with the Polysorbate 20 data being somewhat ambiguous due to the initial fibril formation observed, although it was clear than most of the compound was in solution at pH 3-6, in contrast to Met-12 in the same vehicle. Therefore, Compound 1 solubilities were looked at in cosolvent-surfactant mixtures, starting at high additive concentrations, and then lower concentrations of one or both of the additives, in a sparsely populated matrix experimental design.

Example 5: Mixed Non-Ionic Surfactant/Cosolvent-Solubility Studies of Compound 1

The combination of 70% PG and 10% Polysorbate 80 resulted in a clear solution which became viscous by pH 3.4, and gelled at pH 5.25, which made it no better than 70% PG, and worse than 10% PS-80.

With 70% PG, 3% PS, the viscosity set in at pH 4.6, but the material was still a gel by pH 5.25.

With 35% PG and 3% PS-80, fibrils appeared in solution as low as pH 2.66, and aggregates were seen in solution at pH 3.48.

35% PG, 10% PS-80 showed no signs of fibrils or aggregates, and appreciable viscosity was seen at pH 4.05, and gelling at pH 5.71 (inferior to 10% PS-80 itself).

10% PG and 10% PS-80 produced a clear solution with low viscosity to pH 4.94, and above pH 5.13 began to precipitate material.

10% PG and 3% PS-80 produced a clear solution to pH 3.16, but some precipitation occurred by pH 3.4.

As stated earlier, solution in 10% Polysorbate 20 appeared to give clear mobile solutions all of the way to pH 7, but even at low pH some fibrils were seen, and these tended to increase in number with increasing pH.

Surprisingly, the combination of 10% PG and 10% Polysorbate 20 resulted in good solubility, with the onset of appreciable viscosity only occurring reproducibly above pH 7, and no visual indications of any precipitation being seen. However, on standing overnight, the solution gelled, and the pH dropped by about 0.2 units. Mild agitation reconverted the gel to a liquid, which could be injected.

3% Polysorbate 20, with 10% PG produced a clear mobile solution to pH 5.3, but dropping the PS-20 to 1% produced fibrils below pH 3.

10% PG was added to the 4%, 2% and 0.5% Poloxamer formulations. With the 4% Poloxamer formulation, there appeared to be a slight improvement, no fibrils seen at low pH, and a clear solution to at least pH 5.36. The 2% Poloxamer 10% PG was equally good with a clear mobile solution to pH 5.74. The 0.5% Poloxamer formulation showed fibrils upon initiation of the titration, and showed some turbidity at pH 3.45, but remained of low viscosity until pH 6.

3%, 1% or no PG was added to 2%, 1% and 0.5% Poloxamer formulations, and stability was measured at pH 4.0, pH 5.5 and pH 7.0, after standing for 3 days at RT, using both visual and filtration (see next Example) assays. Visually, fibrils were observed less frequently in newly made up samples, with them being more likely to be observed with less excipients present, and at higher pH, whereas all of the pH 7. 0 samples were turbid initially, and some had obvious precipitation. All of the pH 4.0 samples were initially not turbid, with only the 0.5% PX, 0% PG showing slight turbidity after the hold. With the pH 5.5 samples, initial slight turbidity was seen in all of the 0% PG samples, and the 1% PG 0.5% PX sample, but after the hold only the lowest excipient sample (0.5% PX 0% PG) showed slight turbidity. A couple of these samples became slightly turbid upon agitation. The filtration assay told a rather different story. With the 2% Poloxamer formulations, all three pH 4 formulations had >98% recovery after filtration, and at pH 5.5 recovery was >96%, and at pH 7.0 recoveries were still 86-93%. In 1% PX formulations at pH 4, recovery was 97-98% after filtration, and at pH 5.5 87-93%, but at pH 7 was only 1-13%. In the 0.5©% PX formulations recovery after filtration at pH 4 was 73-88%, at pH 5.5 12-43%, and at pH 7 there was no recovery after filtration in any of the three samples.

From these experiments, it can be concluded that relatively low amounts of PG as a cosolvent can be moderately helpful with some surfactants, but high concentrations were detrimental, and the predictivity of these formulation effects is not high. In the PX formulations, amounts of PX present and formulation pH are both more important than PG levels. Furthermore, visual read-outs do not necessarily agree with the more reliable filtration assay, and observation of fibrils especially seemed uncorrelated with the amount of filterable drug present.

Example 6: Lower Concentration Non-Ionic Surfactant-Solubility Studies of Compound 1

In vitro, and later, in vivo efficacy experiments demonstrated that Compound 1 is in the range of 3->10-fold more potent at blocking FasL (or retinal detachment)-induced apoptosis in photoreceptor cells. These surprising results allow for the projected human dose to be dropped into the 25-200 μg/eye range, which reduced the maximum required concentration of the formulated drug to 2.0 mg/mL. A further set of experiments was carried out to find optimal formulation conditions at that concentration, with some experiments looking at even lower drug concentrations. This work all looked at either Poloxamer 407 or Polysorbate 20 as the surfactant. Both visible turbidity and visual estimation of viscosity are useful screening observations, but as discussed above, it was found that they do not always indicate the presence of aggregated peptide, and much of the later work assessed solubility by measuring the amount of drug present in a sample before and after passing it through an 0.2 micron PVDF membrane or a PALL 25 mm 0.2 µM Ultipor Nylon 6,6 filter. Turbid or highly viscous solutions were generally difficult, or impossible to filter, and when they could be filtered, often gave very low drug recoveries. Surprisingly some mobile, clear, solutions also showed large losses upon filtration, so satisfactory formulations were defined as those which gave >90% drug recovery after filtration. It should be noted that all solubility measurements with compounds like Compound 1, which form fibrils may only measure kinetic solubility. Fibril formation may be very slow under many sets of conditions, and one may be measuring solubility of metastable solutions, where a true thermodynamic solubility, relative to the most stable possible fibril form may take days to years to fully achieve. However, formulations were routinely held for 24-72 hours before filtration, in order to avoid at least rapid precipitation after formulation.

An initial experiment looked at 1 mg/mL solutions of Compound 1 in 3% PS-20/3% PG and 2% PX/2% PG at pH 4. All produced clear solutions, with no loss of API upon filtration. The next experiment looked at 2 mg/mL in 2% PG and 0.1%, 0.25% and 0.5% PX, as well as 0.5% PG and PX, at pH~3, pH 4, pH 5.5 and pH 7. All appeared clear and mobile except the pH 7, 0.1% PX sample which was slightly turbid, and apparently mobile, but that produced no recovery when filtered. The pH 5.5 recovery there was only 78%, and at pH 4.0 92%. Higher amounts of PX led to complete recovery at pH 3 and 4.0, 93-97% at pH 5.3, and 88-92% at pH 7.0. The high and low PG 0.5% PX were essentially identical, suggesting PG is not very important in this area of the formulation manifold.

Since, during these experiments quite large pH changes were occasionally seen on prolonged standing, a similar experiment with 2.0 mg/mL Compound 1, and 0.25% PX. 2% PG was run at pH 3, 4, 5.5 and 7, whilst comparing self-buffered material (HCl salt titrated with NaOH) versus 10 mM histidine, acetate and citrate buffers, with analysis by filtration assay. The acetate buffer was at least as good a self-buffered material at all pHs, the histidine buffer was marginally worse, and the citrate buffer was markedly inferior at all three of the higher pHs, with only 75% recovery at pH 4, versus 91% for histidine buffer, 92% unbuffered, and 97% for acetate buffer. Acetate buffer was then standardized on.

To examine the effects of isotonicity agents, pH 4 and pH 5.5 10 mM acetate buffered solutions at 2 mg mL Compound 1, with 0.25% PX were examined with 0.5% and 2% PG. 4.5% mannitol, 2% glycerin and 0.8% aqueous sodium chloride. All gave 98-99% recovery at pH 4.0 and 90-94% recovery at pH 5.5, except for the sodium chloride samples, which had recoveries of 89% and 79% at the two pHs. All were in the 230-310 mOsm/L range except the 0.5% PG which was rather hypotonic. Using 10 mM acetate buffer and 4.5% mannitol as isotonicity agent, 2 mg/mL of Compound 1, and pH 4.0 and 5.5, five surfactant conditions were looked at. They were no surfactant, 0.1% PS-20, 0.1% PS-20 plus 0.25% PX, 0.25% PX, and 0.4% PX. The no surfactant gave 0% filtered at high pH and 23% at pH 4.0, and the 0.4% PX and 0.25% PX/0.1% PS-20 mixture gave complete recovery at pH 4.0 and 95% and 91% respectively at pH 5.5. The 0.25% PX was somewhat inferior with 96% and 91% respectively and the 0.1% PS rather inferior in turn with 90% and 65% recovery at pH 4 and 5.5 respectively.

As the isotonicity experiment had suggested hydrochloride may be poor for solubility, an experiment was made using 2 mg/mL of the triacetate salt of Compound 1. Because of the weak acidity of acetic acid, the inherent pH of this salt at 2 mg/mL in water is 3.4-3.6, but despite that samples were dissolved up in 10 mM acetic acid, 4.5% mannitol, and 0.4%, 0.5%, 0.6%, 0.8% and 1.0% PX or 0.4%, 0.5%, 0.75%, 1.0% and 1.5% PS-20, and the pH was adjusted to 4.0 or 5.5. All samples with unadjusted pH (3.4-3.6) showed >97% recovery after filtration, and >98% at pH 4. At pH 5.5, 0.4 and 0.5% PX had 96% recovery, and higher PX concentrations produced 98-99% recovery, whereas the PS-20 formulations were all 92-94% recovery at that pH. From these experiments, an optimized formulation could contain less PX than a similar PS-20 based formulation, but PS-20 is still acceptable, and may avoid some potential issues of PX, even when given at higher concentrations.

Example 7: In Vitro Efficacy of Compound 1

Cell Culture.

The 661W photoreceptor cell line was generously provided by Muayyad Al-Ubaidi (Department of Cell Biology, University of Oklahoma Health Sciences Center, Oklahoma City, Okla.). The 661W cell line is a photoreceptor line that has been immortalized by the expression of SV40-T antigen under control of the human interphotoreceptor retinol-binding protein (IRBP) promoter (Al-Ubaidi et al., *J Cell Biol.*, 119(6):1681-1687 (1992), herein incorporated by reference in its entirety). 661W cells express cone photoreceptor markers, including blue and green cone pigments, transducin, and cone arrestin (Tan et al., *Invest Ophthalmol Vis Sci.*, (3):764-768 (2004), herein incorporated by reference in its entirety), and can undergo caspase-mediated cell death (Kanan et al., *Invest Ophthalmol Vis Sci.*, 48(1):40-51 (2007), herein incorporated by reference in its entirety).

The 661W cell line was maintained in Dulbecco's modified Eagle's medium containing 10% fetal bovine serum, 300 mg/L glutamine, 32 mg/L putrescine, 40 µL/L β-mercaptoethanol, 40 µg/L hydrocortisone 21-hemisuccinate, and 40 µg/L progesterone. The media also contained penicillin (90 U/mL) and streptomycin (0.09 mg/mL). Cells were grown at 37° C. in a humidified atmosphere of 5% CO2 and 95% air.

Activity Assays.

Caspase 3, caspase 8 and caspase 9 activities were measured with colorimetric tetrapeptide cleavage assay kits, per the manufacturer's instructions (BioVision, Mountain View, Calif.). Total (66 W/retinal) protein was extracted as per a previously published protocol (Zacks et al., *IOVS*, 44(3): 1262-1267 (2003), herein incorporated by reference in its entirety). One hundred micrograms of total (661W/retinal) protein was incubated with caspase 3 (DEVD-pNA), caspase 8 (IETD-pNA) or caspase 9 substrates (LEHD-pNA) at 200 µM final concentration for 60 minutes. Absorbance was measured at 405 nm in a microplate reader (Spectra-MAX 190, Molecular Devices, Sunnyvale, Calif.). As a negative control, (661W/retinal) protein was incubated with assay buffer without the tetrapeptide. A second negative control was used in which assay buffer alone was incubated with the tetrapeptide. As a positive control, purified caspase 3, caspase 8, or caspase 9 was incubated with the tetrapeptide alone.

Previous experiments conducted during development of the present invention demonstrated that Fas signaling plays a critical role in caspase 8 activation and photoreceptor apoptosis in vivo.

661W cells were treated with a FasL. Addition of the FasL resulted in cell death. Activity of caspase 8 measured in 661W cell lysates increased with increasing concentration of FasL, peaking with the 500 ng/ml dose. 661W cells were treated with 500 ng/ml FasL and measured activity levels at various time points. Caspase 8 activity was significantly increased at 48 hours in 661W cells exposed to FasL. Caspase 8 activity is reliably increased in a dose-dependent manner by 20-30% in different runs.

The assay system described above was used as an in vitro screening system to find potential inhibitors of the Fas-induced Caspase 8 activation pathway. When Met-12 (tri-hydrochloride salt) was tested in this 661W cell assay, it showed a dose dependent reduction in FasL-induced caspase 8 activation, maximizing at 10 µM, where, depending on the assay, caspase 8 activation is reduced to within 0-25% of baseline. This activity is very dependent on the formulation in which the Met-12 peptide is delivered. The final formulation for Met-12 was diluted 1000-fold for this assay, and to get to the top of the dose curve, which is normally 100 µM, one uses lesser dilutions. Under these circumstances, maximal dose potency was seen with a neat DMSO solution, which delivered the Met-12 peptide as a clear, mobile, liquid, where the apparent pH is well below 3.0. When aqueous based formulations were tried, even where there was no visual evidence of precipitation or aggregation prior to the material being added to the test wells, the formulations showed considerably less dose potency, with the maximum inhibition not being achieved until the 50-100 µM doses.

This is strongly suggestive that regardless of the final physical form in the test wells, aggregation in the dosing solution leads to species with much less available drug, even in these cellular assays, than do true solutions being diluted into the exact same conditions, where presumably they have the same intrinsic potential solubility. By far the most likely explanation for this is that the preformed aggregates in the non-solutions are kinetically and thermodynamically stable enough not to disaggregate into solution at an optimal rate during the duration of the test, whereas the solutions when diluted into the test wells either do not form aggregates, or more likely form different aggregates, which dissolve up more easily. The principal reason for the aggregates being different would be that the peptide is at minimum somewhat less concentrated form when it is moved from its pH or cosolvent-boosted soluble form to a 99% aqueous milieu at pH 7.4. However, since efficient mixing is unlikely in the test wells, and impossible in the eye, and, as discussed below, solvating protons (low pH) and small molecule solvents, are going to diffuse in water much faster than the hydrophobic and bulky peptides, it is highly probable that these peptides rapidly aggregate in either test wells or vitreous humor immediately after dosing. Thus, although the solution dosing is clearly superior to the suspension/gel dosing, there is no guarantee that it will not still sequester a lot of the peptide as insoluble aggregates, and reduce the effective concentration of the drug in a stochastic fashion when administered.

Unexpectedly, as shown in FIG. 1, when Compound 1 trihydrochloride was tested in this assay as an unbuffered solution in DMSO, as compared to Met-12 (also a trihydrochloride in DMSO), it proved to be 10-fold more potent than Met-12 by $IC_{50}$ determination, and approximately 3-fold more potent measured by the concentration which produced maximal inhibition of FasL-induced caspase 8 activation. The $EC_{50}$ was 0.4 µM, whereas that for Met-12 itself was 4 µM, and maximal inhibition was seen at 3 µM. However, above 3 µM, Compound 1 showed a U-shaped curve, and above 30 µM, appeared to be almost inactive. In contrast Met-12 dosed in the same manner reaches its (slightly greater) maximum efficacy at 10 µM, and then has only a slight rebound loss of potency out to 100 µM. (See FIG. 1; Caspase 8 activity after 48 hours following treatment with human recombinant FasL after pre-treatment with Met-12 and Compound 1) 0% is the level of caspase 8 Activity of untreated controls. 100% is set to caspase 8 activity of controls only treated with FasL.

As the mechanism of action of FasL involves a trivalent ligand trimerization of the Fas receptor, it is very difficult to see how univalent Met-12 derivatives could have mixed agonist-antagonist dose curves, and it is believed that the loss of potency is a solubility artifact of the assay. However, the unexpected increase in dose potency for Compound 1 should allow for one to give lower amount of the drug than required for Met-12 itself, which in turn reduces the solubility requirements for the peptide formulation for intravitreal injection.

Figure 2:
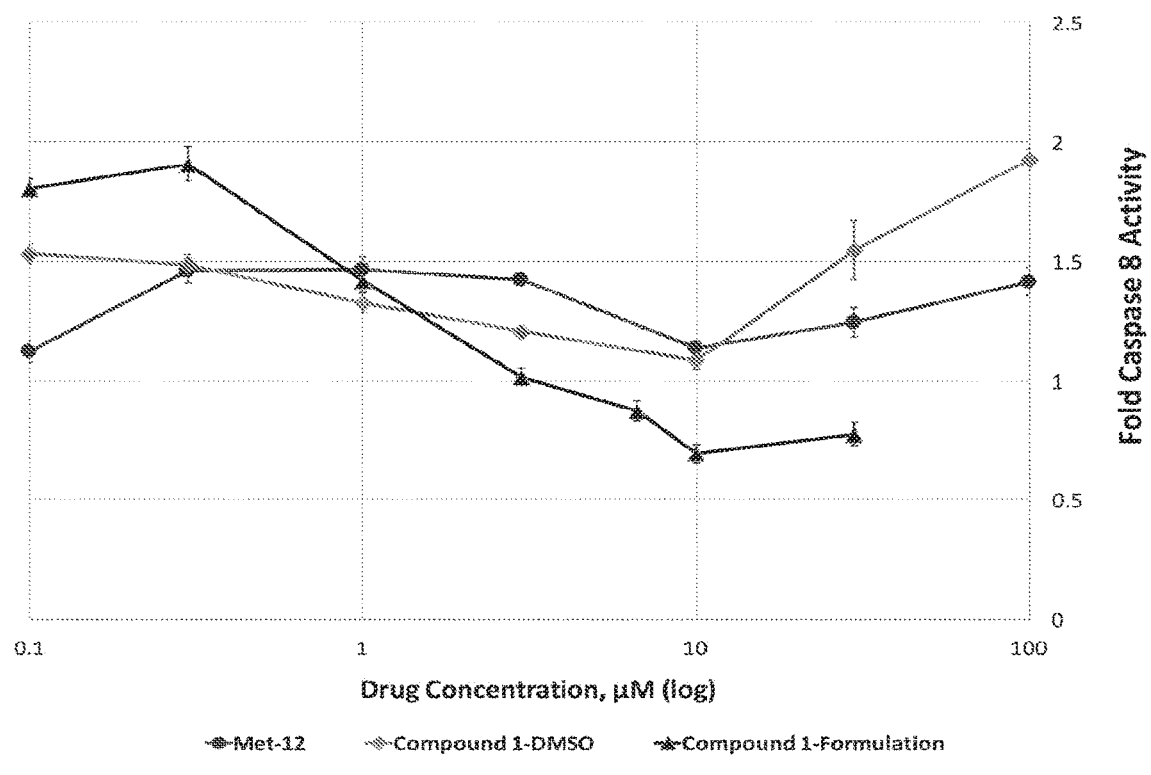
FIG. 2 shows a graph depicting blockade of Fas-induced caspase 8 activation by Met-12 and Compound 1 trihydrochloride in 661W cells. 661W cells were pretreated for 1 hr with various amounts of Met-12 in DMSO (circle), Compound 1 in DMSO (20 mg/mL diamond) and Compound 1 in a 2% Polysorbate (PS) 20, 2% propylene glycol (PG) pH 4 formulation (triangle), all formulations at a 10 mg/mL concentration. The cells were then treated with FasL (500 ng/mL) and Caspase 8 activity was measured at 48 hours after treatment with FasL.

The data shown in FIG. 2 is consistent with the above explanation. It shows once again that Compound 1 trihydrochloride in DMSO (20 mg/mL) is somewhat more dose potent than Met-12, but that it again becomes inactive at higher concentrations. In contrast, when made up at a concentration of 10 mg/mL in a clear, filterable presumably micellar solution of 2% Polysorbate 20 and 2% PG at pH 4, Compound 1 trihydrochloride is both considerably more dose potent, but also more efficacious than Met-12 or Compound 1 in DMSO. Furthermore, there is very little loss of maximum efficacy at the top dose of 30 µM tested in this assay. This surprising result shows the ability to formulate Compound 1 in surfactants can lead to a large boost in drug efficacy.

Figure 3:
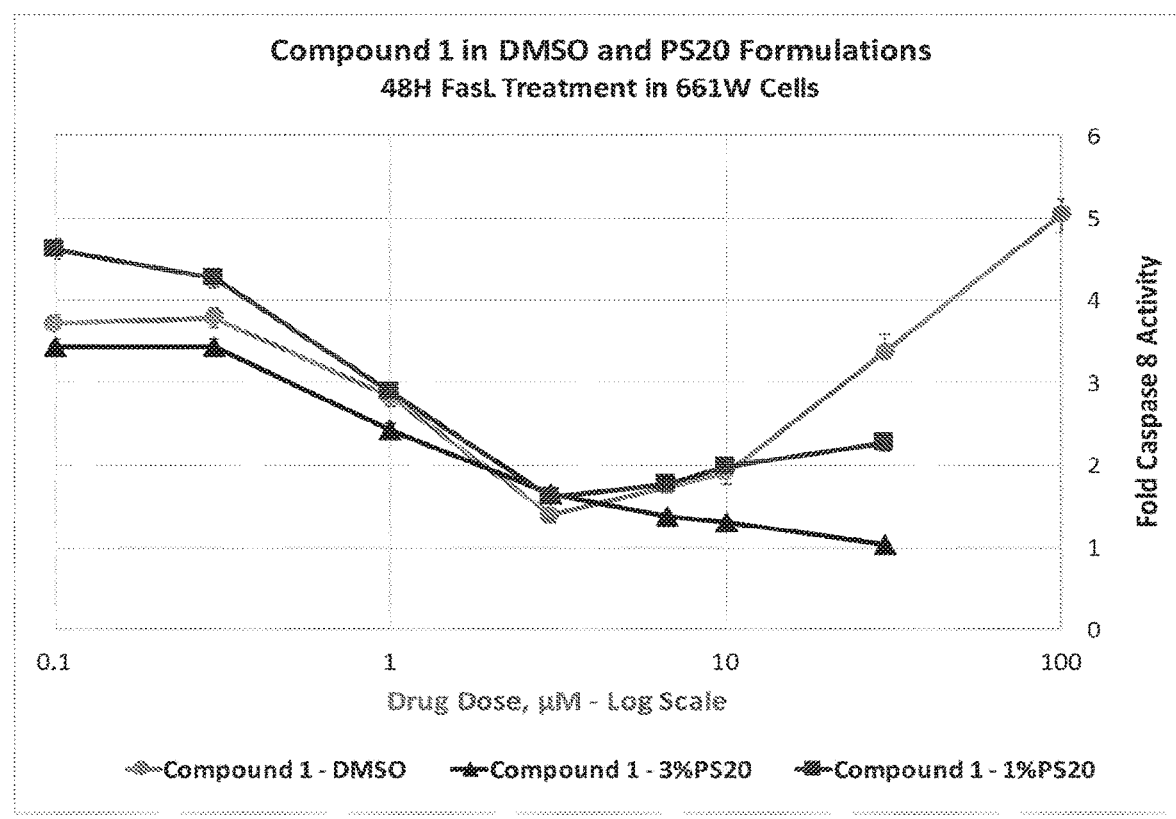
FIG. 3 shows a graph depicting blockade of Fas-induced caspase 8 activation by Compound 1 trihydrochloride in 661W cells. 661W cells were pretreated for 1 hr with various amounts of Compound 1 in DMSO (20 mg/mL) (circle), and in a 3% Polysorbate 20, 3% propylene glycol pH 4 formulation (triangle), and in a 1% Polysorbate 20, 3% propylene glycol pH 4 formulation (diamond), all formulations at a 10 mg/mL concentration. The cells were then treated with FasL (500 ng/mL) and Caspase 8 activity was measured at 48 hours after treatment with FasL.

FIG. 3 compares a 20 mg/mL DMSO solution with two Polysorbate formulations of Compound 1 trihydrochloride containing 1% and 3% PS-20 and 3% PG at pH 4 with all at 10 mg/mL concentration. All 3 show similar efficacy in this case at lower concentrations, but the 1% PS-20 only shows a weak loss of activity from its most potent 3 µM concentration, all of the way out to 30 µM, whereas the 3% PS shows continued increase in activity all of the way to 30 µM, the top dose tested.

Figure 4:
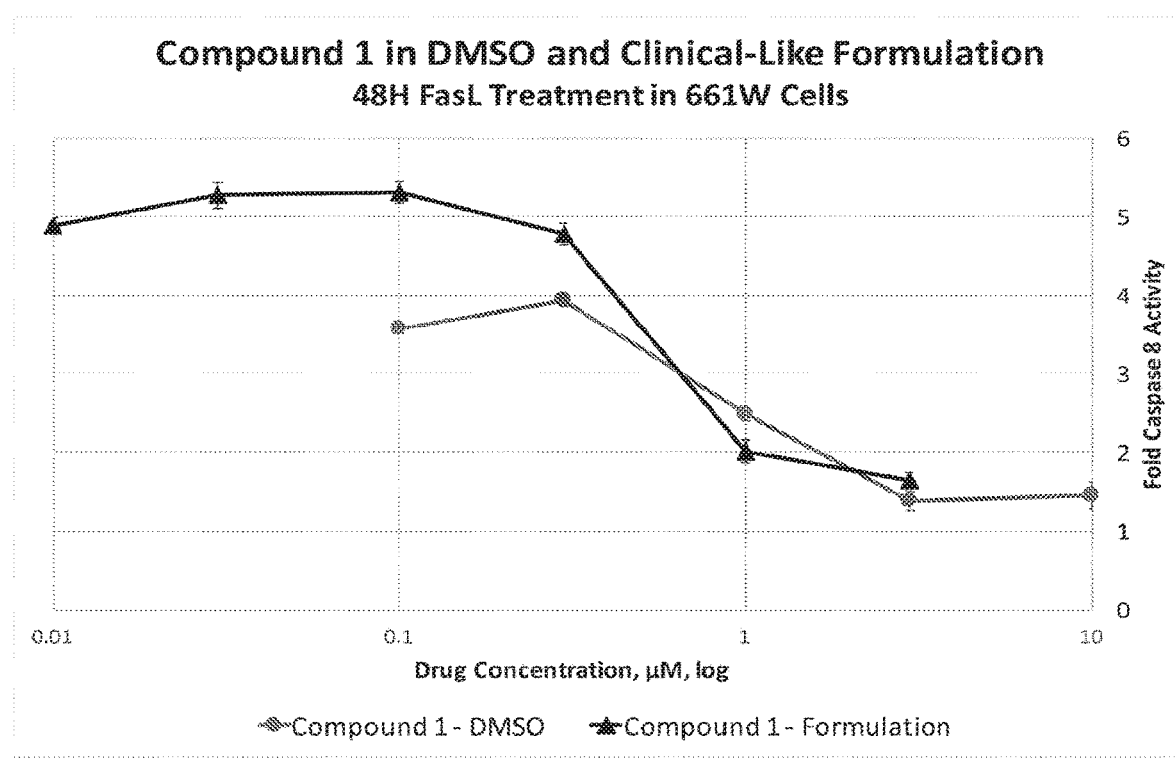
FIG. 4 shows a graph depicting blockade of Fas-induced caspase 8 activation by Compound 1 trihydrochloride in 661W cells. 661W cells were pretreated with various amounts of Compound 1 trihydrochloride in DMSO (20 mg/mL) (circle), and in an 0.4% Polysorbate-20, 4.5% mannitol, 10 mM acetate pH 4 formulation (triangle), at a 2 mg/mL concentration. The cells were then treated with FasL (500 ng/mL) and Caspase 8 activity was measured at 48 hours after treatment with FasL.

In FIG. 4 an optimized formulations of Compound 1 trihydrochloride, at 2 mg/mL in pH 4 10 mM acetate buffer, 4.5% mannitol and 0.4% PS-20 (dark triangles) is compared to 20 mg/mL Compound 1 trihydrochloride in DMSO (light circles) in 661W cells. The trihydrochloride in DMSO shows the usual U-shaped curve with a maximal effect at 3 µM, and considerable rebound at higher concentrations. The formulation could only be tested to 10 µM, due to its low concentrations, but shows similar efficacy to the DMSO solution.

A likely explanation for greater efficacy seen with the micelle formulations is that the peptide solubility is maintained for a longer period of time by the self-assembling propensity of the surfactant, which is only slowly affected by dilution and dispersion, in sharp contrast to pH gradients or small molecule cosolvents. Thus the micelles and the peptide are more widely dispersed into the aqueous medium, before the peptide is released into the aqueous medium, because the micelles only fall apart slowly, whereas in a cosolvent, or highly acidic solution, the solubilizing factor (hydrogen ions, small molecule), is very rapidly diluted into the aqueous medium, before the peptide has any real chance to disperse beyond the areas into which the injection directly placed it. This will cause the peptide to disperse less efficiently from solution formulations and form more inactive aggregates, than it will from a micellar formulation.

Example 8: Rabbit Intravitreal Ocular Pharmacokinetic Study with Compound 1

This study was conducted to determine the concentrations of Compound 1 in vitreous humor (VH) and retina tissue following intravitreal injections of male Dutch Belted rabbits. Concentrations were determined in tissues at 24, 72, 168, and 240 hours post-dose of a 50 µL bilateral intravitreal (IVT) dose.

The study design is summarized in Table 1.

TABLE 1

Study design.

| Group | Formulation | Dose and Route | Terminal Timepoints (Blood and Ocular Tissues) | Matrices Collected | Matrices Analyzed |
|---|---|---|---|---|---|
| 1 (n = 8) | 2 mg/mL Compound 1 triacetate in 4.5% mannitol, 10 mM acetic acid, 0.4% poloxamer 407, pH 4.5 | 50 µL/eye 0.1 mg/eye IVT | 24, 72, 168, and 240 hours postdose (n = 2/timepoint) | Vitreous Humor and Retina | Vitreous Humor and Retina |
| 2 (n = 8) | 0.5 mg/mL Compound 1 triacetate in 4.5% mannitol, 10 mM acetic acid, 0.4% poloxamer 407, pH 4.5 | 50 µL/eye 0.025 mg/eye IVT | 24, 72, 168, and 240 hours postdose (n = 2/timepoint) | Vitreous Humor and Retina | Vitreous Humor and Retina |
| 3 (n = 8) | 0.5 mg/mL Compound 1 triacetate in 4.5% mannitol, 10 mM acetic acid, 0.1% poloxamer 407, pH 4.5 | 50 µL/eye 0.025 mg/eye IVT | 24, 72, 168, and 240 hours postdose (n = 2/timepoint) | Vitreous Humor and Retina | Vitreous Humor and Retina |
| 4 (n = 8) | 1 mg/mL Compound 1 triacetate in 4.5% mannitol, 10 mM acetic acid, 0.4% polysorbate 20, pH 4.5 | 50 µL/eye 0.05 mg/eye IVT | 24, 72, 168, and 240 hours postdose (n = 2/timepoint) | Vitreous Humor and Retina | Vitreous Humor and Retina |

Test system included the following:
Species/Strain/Gender: Male Dutch Belted Rabbits
Supplier: Covance Research Products, Inc.
Age Range: 4 to 5 months
Weight at Receipt (Range of Weights): 1.51-1.85 kg
Administration Route: Intravitreal (IVT) injection
Duration of Treatment: Single Dose per eye
Formulation Concentrations: 2.0. 1.0, and 0.5 mg/mL Compound 1 triacetate
Dose Volume: 50 µL per eye An intravitreal (IVT) injection ocular dose of 50 µL was administered to the globe of each of Dutch Belted rabbit eye.

At the respective time points the rabbits were euthanized by intravenous barbiturate overdose, and eyes were enucleated and snap frozen. Vitreous humor and retina were collected from all animals and analyzed for Compound 1 by LC-MS/MS Calculations:
Percent Coefficient of Variation:
Used as an estimate of precision.
Percent Coefficient of Variation (% CV)=(Standard Deviation/average value)*100

Quadratic Least Squares Analysis:
The standard curve fit was determined using a quadratic equation with $1/x^2$ weighting:

$$y = a2 + bx + c$$

where: y=peak area ratio of the calibration standards to internal standard
x=concentration of the calibration standard
a=quadratic coefficient of $x^2$
b=quadratic coefficient of x
c=the constant as the y-intercept of the calibration curve Quadratic Analyte Concentration:
The concentration of analyte is calculated using the calibration curve parameters calculated above and then solving for the value of x.

Results

Retina and VH concentrations are found in Tables 2 and 3 below, and graphically represented in FIGS. 1 and 2. Pharmacokinetic parameters were calculated where appropriate and are summarized in Tables 4 and 5 below.

TABLE 2

Concentrations of Compound 1 in Dutch Belted retina.

| Group | Sample ID | Time Point | Eye | Retina Mass (g) | Amount of Diluent Added (μL) | Total Volume (μL) | Calculated Concentration (ng/mL) | Calculated Concentration (ng/g) | Mean (ng/g) | SD | % CV |
|---|---|---|---|---|---|---|---|---|---|---|---|
| 1 | A | 24 hr | OD | 0.04327 | 173 | 216 | 62.0 | 309 | 596 | 872 | 146 |
|   |   |   | OS | 0.04312 | 172 | 215 | <LLOQ | <LLOQ |   |   |   |
|   | B |   | OD | 0.06310 | 252 | 315 | 378 | 1890 |   |   |   |
|   |   |   | OS | 0.05021 | 201 | 251 | 36.7 | 183 |   |   |   |
|   | A | 72 hr | OD | 0.04984 | 199 | 249 | <u>25300</u> | <u>126000</u> | 1630 | 1500 | 92.0 |
|   |   |   | OS | 0.04052 | 162 | 203 | 224 | 1120 |   |   |   |
|   | B |   | OD | 0.04274 | 171 | 214 | 664 | 3320 |   |   |   |
|   |   |   | OS | 0.04199 | 168 | 210 | 89.3 | 447 |   |   |   |
|   | A | 168 | OD | 0.04319 | 173 | 216 | 103 | 515 | 354 | 332 | 93.8 |
|   |   |   | OS | 0.04484 | 179 | 224 | <LLOQ | <LLOQ |   |   |   |
|   | B |   | OD | 0.04184 | 167 | 209 | 147 | 734 |   |   |   |
|   |   |   | OS | 0.03689 | 148 | 185 | 33.5 | 168 |   |   |   |
|   | A | 240 | OD | 0.03929 | 157 | 196 | 112 | 559 | 490 | 114 | 23.3 |
|   |   |   | OS | 0.04716 | 189 | 236 | 82.2 | 411 |   |   |   |
|   | B |   | OD | 0.04788 | 192 | 240 | 122 | 612 |   |   |   |
|   |   |   | OS | 0.05603 | 224 | 280 | 75.2 | 376 |   |   |   |
| 2 | A | 24 hr | OD | 0.03837 | 153 | 191 | 56.8 | 283 | 169 | 121 | 71.6 |
|   |   |   | OS | 0.03881 | 155 | 194 | 35.4 | 177 |   |   |   |
|   |   |   | OD | 0.03939 | 158 | 197 | 43.2 | 216 |   |   |   |
|   | B |   | OS | 0.04028 | 161 | 201 | <LLOQ | <LLOQ |   |   |   |
|   |   |   | OD | 0.04784 | 191 | 239 | 63.6 | 318 |   |   |   |
|   | A | 72 hr | OS | 0.04461 | 178 | 223 | <LLOQ | <LLOQ | 223 | 173 | 77.6 |
|   | B |   | OD | 0.03850 | 154 | 193 | 36.0 | 180 |   |   |   |
|   |   |   | OS | 0.03466 | 139 | 174 | 78.6 | 395 |   |   |   |
|   | A |   | OD | 0.04639 | 186 | 232 | 503 | 2520 |   |   |   |
|   |   | 168 | OS | 0.04044 | 162 | 202 | 56.7 | 283 | 912 | 1070 |   |
|   | B |   | OD | 0.05231 | 209 | 261 | 82.2 | 410 |   |   | 117 |
|   |   |   | OS | 0.04112 | 164 | 205 | 87.4 | 436 |   |   |   |
|   | A |   | OD | 0.04847 | 194 | 242 | 66.8 | 334 |   |   |   |
|   |   | 240 | OS | 0.04503 | 180 | 225 | 212 | 1060 | 631 | 329 |   |
|   | B |   | OD | 0.04467 | 179 | 224 | 142 | 712 |   |   | 52.1 |
|   |   |   | OS | 0.04772 | 191 | 239 | 83.4 | 418 |   |   |   |
| 3 | A | 24 hr | OD | 0.04893 | 196 | 245 | 24.8 | 124 | 929 | 1450 | 156 |
|   |   |   | OS | 0.04561 | 182 | 228 | 621 | 3100 |   |   |   |
|   |   |   | OD | 0.05029 | 201 | 251 | 28.0 | 140 |   |   |   |
|   | B |   | OS | 0.04463 | 179 | 224 | 69.8 | 350 |   |   |   |
|   | A |   | OD | 0.04474 | 179 | 224 | 33.0 | 165 |   |   |   |
|   |   | 72 hr | OS | 0.04508 | 180 | 225 | <LLOQ | <LLOQ | 68.0 | 82.0 | 121 |
|   | B |   | OD | 0.04974 | 199 | 249 | 21.3 | 107 |   |   |   |
|   |   |   | OS | 0.04698 | 188 | 235 | <LLOQ | <LLOQ |   |   |   |
|   | A |   | OD | 0.04188 | 168 | 210 | 832 | 4170 |   |   |   |
|   |   | 168 | OS | 0.03783 | 151 | 189 | <LLOQ | <LLOQ | 1440 | 1890 | 131 |
|   | B |   | OD | 0.03577 | 143 | 179 | 74.3 | 372 |   |   |   |
|   |   |   | OS | 0.04405 | 176 | 220 | 247 | 1230 |   |   |   |
|   | A |   | OD | 0.03215 | 129 | 161 | 104 | 521 |   |   |   |
|   |   | 240 | OS | 0.04526 | 181 | 226 | <LLOQ | <LLOQ | 192 | 248 | 129 |
|   | B |   | OD | 0.03895 | 156 | 195 | 49.6 | 248 |   |   |   |
|   |   |   | OS | 0.05110 | 204 | 255 | <LLOQ | <LLOQ |   |   |   |
| 4 | A | 24 hr | OD | 0.04033 | 161 | 201 | 32.1 | 160 | 206 | 237 | 115 |
|   |   |   | OS | 0.04551 | 182 | 228 | 109 | 546 |   |   |   |
|   |   |   | OD | 0.03931 | 157 | 196 | 23.6 | 1118 |   |   |   |
|   | B |   | OS | 0.04407 | 176 | 220 | <LLOQ | <LLOQ |   |   |   |
|   | A |   | OD | 0.04616 | 185 | 231 | <LLOQ | <LLOQ |   |   | 1 |
|   |   | 72 hr | OS | 0.04115 | 165 | 206 | 34.4 | 172 | 95.0 | 111 |   |
|   | B |   | OD | 0.04900 | 196 | 245 | 41.5 | 208 |   |   | 117 |
|   |   |   | OS | 0.04991 | 200 | 250 | <LLOQ | <LLOQ |   |   |   |
|   | A |   | OD | 0.03554 | 142 | 178 | <LLOQ | <LLOQ |   |   |   |
|   |   | 168 | OS | 0.03511 | 140 | 175 | 41.0 | 204 | 51.0 |   | ISD |
|   | B |   | OD | 0.05409 | 216 | 270 | <LLOQ | <LLOQ |   | ISD |   |
|   |   |   | OS | 0.04863 | 195 | 244 | <LLOQ | <LLOQ |   |   |   |
|   | A |   | OD | 0.04413 | 177 | 221 | <LLOQ | <LLOQ |   |   |   |
|   |   | 240 | OS | 0.04205 | 168 | 210 | <LLOQ | <LLOQ | 27.3 | ISD | ISD |
|   | B |   | OD | 0.04442 | 178 | 222 | <LLOQ | <LLOQ |   |   |   |
|   |   |   | OS | 0.05194 | 208 | 260 | 21.7 | 109 |   |   |   |

LLOQ = 20.0 ng/mL or 100 ng/g
Values < LLOQ use 0 for statistical determination
ISD = insufficient data for determination
Underlined: Exceeds upper limit of quantitation and outlier, data excluded

TABLE 3

Concentrations of Compound 1 in Dutch Belted vitreous humor.

| Group | Sample ID | Time Point | Eye | Calculated Concentration (ng/mL) | Vitreous Humor Weight (g)* | Calculated Concentration (µg/eye) | Mean (ng/g) | SD | % CV |
|---|---|---|---|---|---|---|---|---|---|
| 1 | A | 24 hr | OD | *104000* | 1.05875 | 110 | 106 | 8.05 | 7.59 |
|   |   |   | OS | *105000* | 1.09135 | 115 |   |   |   |
|   | B |   | OD | *78800* | 1.27841 | 101 |   |   |   |
|   |   |   | OS | *75900* | 1.28441 | 97.5 |   |   |   |
|   | A | 72 hr | OD | *125000* | 0.71978 | 90.0 | 90.4 | 8.07 | 8.93 |
|   |   |   | OS | *104000* | 0.76824 | 79.9 |   |   |   |
|   | B |   | OD | *97700* | 0.94602 | 92.4 |   |   |   |
|   |   |   | OS | *106000* | 0.93764 | 99.4 |   |   |   |
|   | A | 168 hr | OD | 84800 | 1.16490 | 98.8 | 103 | 5.82 | 5.65 |
|   |   |   | OS | 81500 | 1.18636 | 96.7 |   |   |   |
|   | B |   | OD | 92600 | 1.17384 | 109 |   |   |   |
|   |   |   | OS | 88500 | 1.20263 | 106 |   |   |   |
|   | A | 240 hr | OD | 79400 | 1.17233 | 93.1 | 84.2 | 14.9 | 17.7 |
|   |   |   | OS | 87500 | 1.12218 | 98.2 |   |   |   |
|   | B |   | OD | 52900 | 1.22366 | 64.7 |   |   |   |
|   |   |   | OS | 65300 | 1.23536 | 80.7 |   |   |   |
| 2 | A | 24 hr | OD | 22000 | 0.84743 | 18.6 | 22.9 | 2.86 | 12.5 |
|   |   |   | OS | 20400 | 1.19418 | 24.4 |   |   |   |
|   |   |   | OD | 21200 | 1.15.341 | 24.5 |   |   |   |
|   | B |   | OS | 21700 | 1.10663 | 24.0 |   |   |   |
|   |   |   | OD | 21300 | 1.09577 | 23.3 |   |   |   |
|   | A | 72 hr | OS | 1900 | 1.12046 | <u>2.13</u> | 23.6 | 0.379 |   |
|   |   |   | OD | 20000 | 1.16980 | 23.4 |   |   | 1.61 |
|   | B |   | OS | 20600 | 1.16716 | 24.0 |   |   |   |
|   | A |   | OD | 22300 | 1.12460 | 25.1 |   |   |   |
|   |   |   | OS | 20500 | 1.05482 | 21.6 | 23.0 |   | 6.52 |
|   | B | 168 hr | OD | 21600 | 1.05841 | 22.9 |   | 1.50 |   |
|   |   |   | OS | 18400 | 1.21646 | 22.4 |   |   |   |
|   | A |   | OD | 18000 | 1.17848 | 21.2 |   |   |   |
|   |   | 240 hr | OS | 15100 | 1.28698 | 19.4 | 19.5 | 1.28 | 6.56 |
|   | B |   | OD | 14800 | 1.22182 | 18.1 |   |   |   |
|   |   |   | OS | 16000 | 1.20828 | 19.3 |   |   |   |
| 3 | A | 24 hr | OD | 24500 | 1.21473 | 29.8 | 26.0 | 2.73 | 10.5 |
|   |   |   | OS | 20300 | 1.18169 | 24.0 |   |   |   |
|   |   |   | OD | 21100 | 1.23315 | 26.0 |   |   |   |
|   | B |   | OS | 19300 | 1.24396 | 24.0 |   |   |   |
|   | A |   | OD | 214 | 1.19559 | <u>0.256</u> |   |   |   |
|   |   | 72 hr | OS | 18900 | 1.22604 | 23.2 | 22.8 | 0.814 |   |
|   |   |   | OD | 21000 | 1.11298 | 23.4 |   |   | 3.57 |
|   | B |   | OS | 18900 | 1.15681 | 21.9 |   |   |   |
|   | A |   | OD | 21900 | 1.09436 | 24.0 |   |   |   |
|   |   |   | OS | 26100 | 1.08970 | 28.4 | 25.5 | 1.98 | 7.76 |
|   | B | 168 hr | OD | 20700 | 1.18375 | 24.5 |   |   |   |
|   |   |   | OS | 21300 | 1.18491 | 25.2 |   |   |   |
|   |   |   | OD | 16700 | 1.18857 | 19.8 |   |   |   |
|   | A |   | OS | 18200 | 1.19607 | 21.8 |   |   |   |
|   |   | 240 hr | OD | 16200 | 1.18248 | 19.2 | 20.4 | 1.13 | 5.54 |
|   | B |   | OS | 16700 | 1.23788 | 20.7 |   |   |   |
| 4 | A | 24 hr | OD | 44000 | 1.08887 | 47.9 | 46.8 | 2.55 | 5.45 |
|   |   |   | OS | 40000 | 1.08052 | 43.2 |   |   |   |
|   |   |   | OD | 38500 | 1.2.1775 | 46.9 |   |   |   |
|   | B |   | OS | 41600 | 1.17967 | 49.1 |   |   |   |
|   | A |   | OD | 39600 | 1.10963 | 43.9 |   |   |   |
|   |   | 72 hr | OS | 33500 | 1.14187 | 38.3 | 32.5 | 10.2 | 31.4 |
|   |   |   | OD | 23100 | 1.02867 | 23.8 |   |   |   |
|   | B |   | OS | 21700 | 1.09956 | 23.9 |   |   |   |
|   | A |   | OD | 25900 | 1.04704 | 27.1 |   |   |   |
|   |   |   | OS | 21000 | 1.22612 | 25.7 | 25.6 |   | 4.38 |
|   | B | 168 hr | OD | 19900 | 1.22735 | 24.4 |   | 1.12 |   |
|   |   |   | OS | 20000 | 1.26320 | 25.3 |   |   |   |
|   | A |   | OD | 19800 | 1.10090 | 21.8 |   |   |   |
|   |   | 240 hr | OS | 158 | 1.12301 | <u>0.177</u> | 19.4 | ISD | ISD |
|   | B |   | OD | 12500 | 1.35282 | 16.9 |   |   |   |
|   |   |   | OS | 177 | 1.38049 | <u>0.244</u> |   |   |   |

LLOQ = 50.0 ng/mL
*assume density of 1.00 g/mL
Underlined: Suspected outlier, data not included in statistics
ISD = insufficient data for determination
Italics: Result exceeds upper limit of quantitation, estimated data.

Figure 5A:
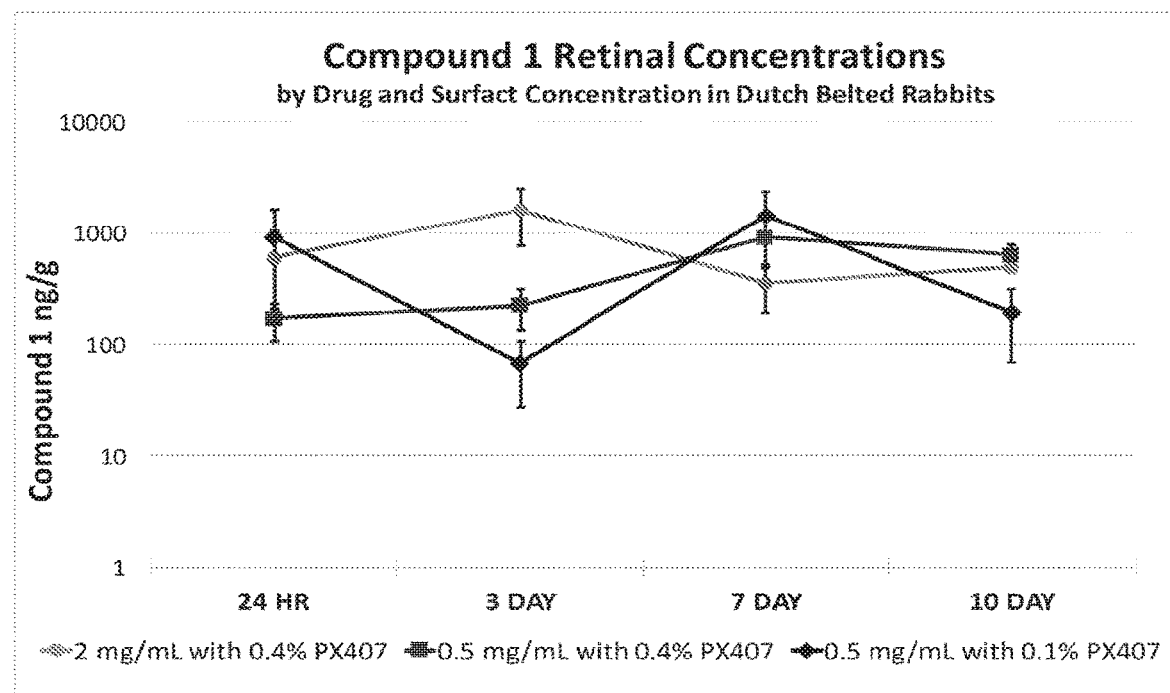
FIG. 5a depicts a logarithmic graph of rabbit retina concentrations of Compound 1 delivered intravitreally in three Poloxamer formulations.
Figure 5B:
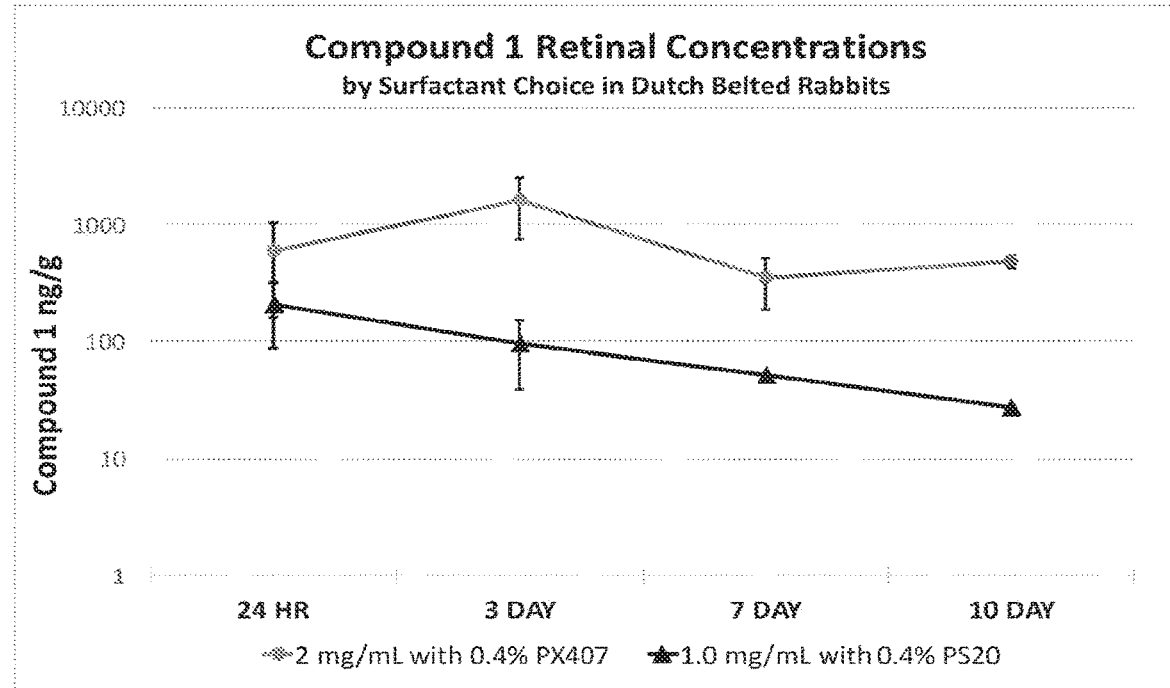
FIG. 5b depicts a logarithmic graph of rabbit retina concentrations of Compound 1 delivered intravitreally to compare a Poloxamer 407-based formulation with a Polysorbate-20 based formulation over time.
Figure 6A:
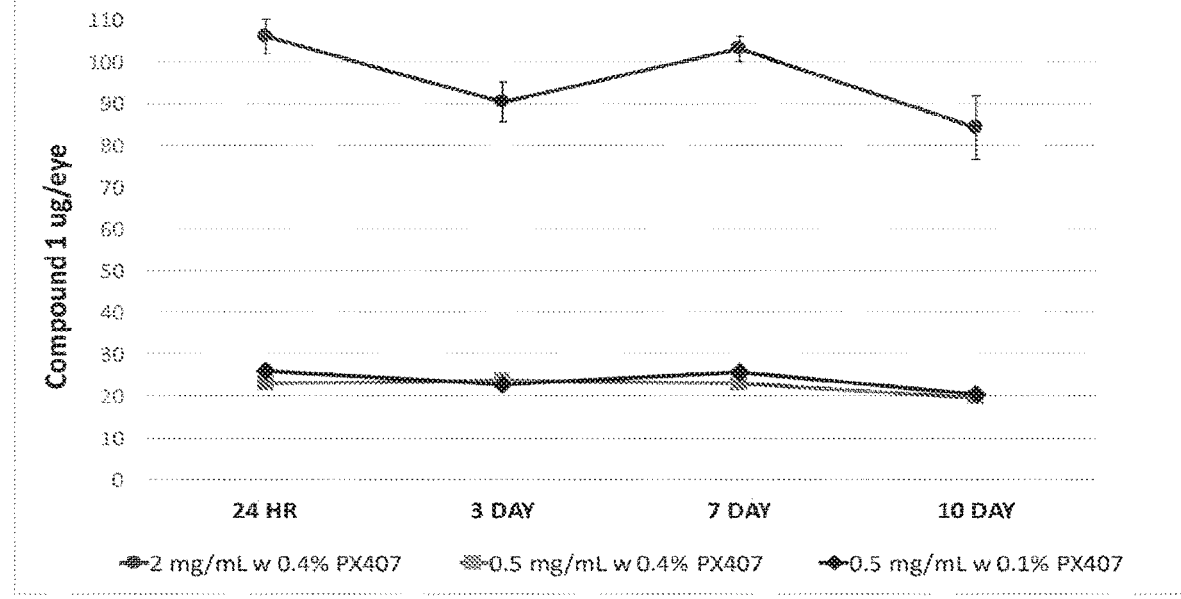
FIG. 6a depicts linear graph of rabbit vitreous humor (VH) concentrations over time of Compound 1 delivered intravitreally in three Poloxamer formulations with varying concentrations of surfactant (0.4% or 0.1%) and varying concentrations of Compound 1 (2 mg/mL vs 0.5 mg/mL).
Figure 6B:
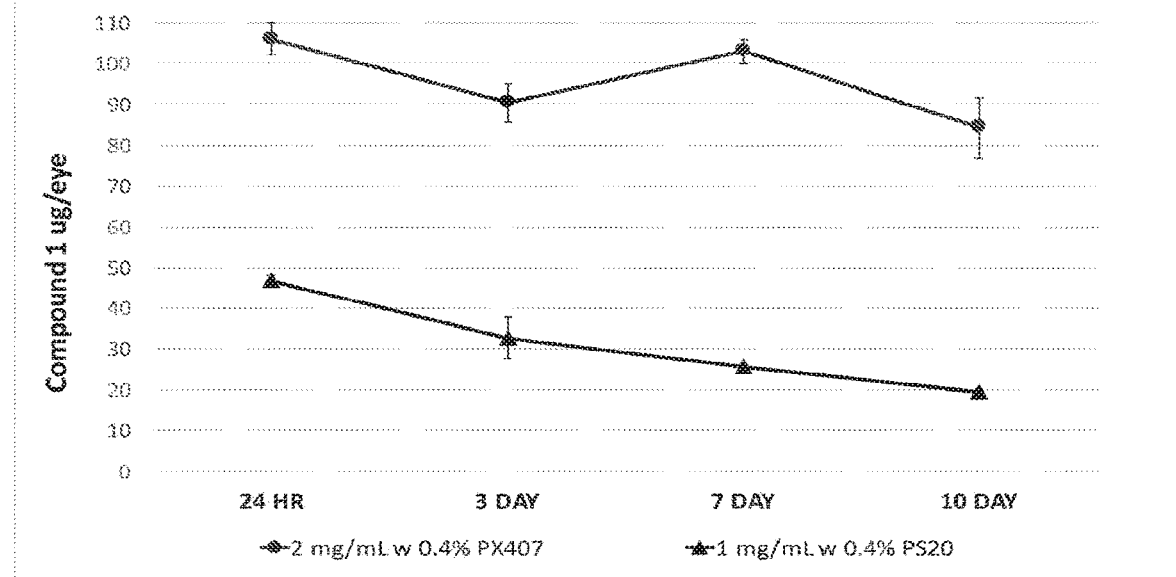
FIG. 6b depicts a linear graph of rabbit VH concentrations over time with different choice of surfactant (0.4% Poloxamer 407 vs. 0.4% Polysorbate 20) and varying amount of Compound 1 (2 mg/mL vs 1 mg/mL).

Results of this study in both retina and vitreous humor are shown in FIG. 5 (A+B) and FIG. 6 (A+B) respectively. Retinal concentrations of Compound 1 were variable with coefficient of variability (% CV) ranging from 52 to 156 percent over the time-course of the study for all groups. Retina $T_{max}$ was noted at 72 (3 days) or 168 (7 days) hours post-administration for the three Poloxamer formulations, but was not dose dependent, while retina $T_{max}$ for the Polysorbate formulation was 24 hours post-administration. Retina $AUC_{0-last}$ followed a similar variable pattern as $C_{max}$. Retina. $T_{1/2}$ for Compound 1 could only be calculated for the 2 mg/mL Poloxamer (168 hours) and 1 mg/mL Polysorbate (199 hours) retina data.

Analysis of vitreous humor for Compound 1 indicated the concentration to be relatively consistent within each timepoint for the Poloxamer formulations. When normalized by weight of the VH collected, a theoretical total of Compound 1 was calculated. The total amount of Compound 1 injected into each rabbit eye was 100 µg (2 mg/mL*50 µL) or 25 µg (0.5 mg/mL*50 µL) for the Poloxamers and 50 µg (1 mg/mL*50 µL) for the Polysorbate group. The lowest mean concentration for all groups was at 10 days. Mean Compound 1 remaining in the VH for Group 1 (100 µg) ranged from 84.2 µg to 106 µg 24 hours to 10 days post-IVT administration. Mean Compound 1 remaining in the VH for Group 2 (25 µg) ranged from 19.5 µg to 23.0 µg 24 hours to 10 days post-IVT administration. Mean Compound 1 remaining in the VH for Group 3 (25 µg) ranged from 26.0 µg to 20.4 µg 24 hours to 10 days post-IVT administration. Mean Compound 1 remaining in the VH for the Polysorbate Group 4 (50 µg) ranged from a high of 46.8 µg at 24 hours to 19.4 µg at 10 days post-IVT administration. The Polysorbate group was the only formulation with a notable decrease in Compound 1 concentrations with time. Yet, in all groups substantial amounts of intact drug were detected 10 days post-administration.

Calculation of pharmacokinetic parameters for Compound 1 in VH indicated a $T_{max}$ of 24 or 72 hours post IVT administration with a $C_{max}$ closely matching the total amount of drug administered for each group (Table 4). $AUC_{0-last}$ was nearly dose proportional between the Poloxamer groups with Group 1 (2 mg/mL) having an approximate four times greater AUC than that of Groups 2 and 3 (both 0.5 mg/mL). The Polysorbate group (1 mg/mL) was less than dose proportional relative to the Poloxamer groups but it can be readily explained as it was the only group that had a notable decrease in Compound 1 VH concentration over the course of the study. $T_{1/2}$ for the Polysorbate group was 183 hours with a good linear fit whereas the $t_{1/2}$ for the Poloaxmer groups was >900 hours with a less than optimal linear fit.

TABLE 4

Pharmacokinetic Parameters for Compound 1 in Vitreous Humor.

| Parameter | 2 mg/mL Poloxamer | 0.5 mg/mL Poloxamer | 0.5 mg/mL Reduced Poloxamer | 1 mg/mL Polysorbate |
|---|---|---|---|---|
| $T_{max}$ (h) | 24 | 72 | 24 | 24 |
| $C_{max}$ (µg/eye) | 106 | 23.6 | 26.0 | 46.8 |
| Terminal $t_{1/2}$ (h) | 1028* | 994* | 911* | 183 |
| $AUC_{0-last}$ (µg*h/eye) | 22000 | 5150 | 5460 | 6870 |

*R2 < 0.7

TABLE 5

Pharmacokinetic Parameters for Compound 1 in Retina.

| Parameter | 2 mg/mL Poloxamer | 0.5 mg/mL Poloxamer | 0.5 mg/mL Reduced Poloxamer | 1 mg/mL Polysorbate |
|---|---|---|---|---|
| $T_{max}$ (h) | 72 | 168 | 168 | 24 |
| $C_{max}$ (ng/g) | 1630 | 912 | 1924 | 275 |
| Terminal (h) | 168 | NC | NC | 199 |
| $AUC_{0-last}$ (ng*h/g) | 203000 | 129000 | 219000 | 44600 |

NC—not calculated

In summary, the Compound 1 when administered IVT in either the Poloxamer or Polysorbate formulations showed no signs of irritation or tolerability issues over the 10 day course of the study. The Compound 1 when administered IVT as a Poloxamer formulation does not readily diminish in concentration for a period of up to 10 days, and likely longer, in either the retina or VH. The Compound 1 when administered as a Polysorbate formulation demonstrated a clear albeit slow decrease in concentration over the 10 day study time course, suggesting that intravitreal pharmacokinetics may be controllable within certain parameters by careful choice of the non-ionic surfactant used.

Example 9: Rat Ocular Pharmacokinetic Study with Compound 1

This study was conducted to determine the concentrations of Compound 1 trihydrochloride in vitreous humor and retina tissues following intravitreal injections of Brown Norway rats. Concentrations were determined in tissues at 24 (Group 1), and 72 hours (Groups 1 and 2) post-dose of a 5 µL bilateral intravitreal (IVT) dose.

The study design is summarized in Table 6.

TABLE 6

Study design.

| Group | Formulation | Dose and Route | Terminal Timepoints (Blood and Ocular Tissues) | Matrices Collected | Matrices Analyzed |
|---|---|---|---|---|---|
| 1 (n = 8) | 0.06 mg/mL Compound 1 in 4.5% mannitol, 10 mM acetic acid, 0.4% poloxamer 407, pH 4.5 | 0.3 µg/eye IVT | 24 and 72 hours post-dose (n = 4/time point) | Vitreous Humor and Retina | Vitreous Humor and Retina |
| 2 (n = 8) | 0.06 mg/mL Compound 1 in 4.5% mannitol, 10 mM acetic acid, 0.4% poloxamer 407, pH 4.5 | 0.3 µg/eye IVT | 72 hours post-dose The retinas from 4 animals will be pooled in 2 samples at 72 hours. | Vitreous Humor and Retina | Vitreous Humor and Retina |

Test system included the following:
Species/Strain/Gender: Norway Brown Rats
Supplier: Charles River, Inc.
Age Range: 1 to 2 months
Weight at Receipt (Range of Weights): 165.9-181.2 g
Administration Route: Intravitreal (IVT) injection
Duration of Treatment: Single dose per eye
Formulation Concentrations: 0.06 mg/mL ONL-1204 triacetate
Dose Volume: 5 pJL per eye Harvesting of Ocular Tissues Rats were euthanized by intravenous barbiturate overdose, and eyes were enucleated and snap frozen. Vitreous humor (VH) and retina were collected from all animals and analyzed for Compound 1 by LC-MS/MS.

Results

Ocular Tissue Concentrations

Compound 1 Trihydrochloride Concentrations in Brown Norway Rat Retina and Vitreous Humor Unknowns

TABLE 7

Concentrations of Compound 1 in Brown Norway rat retina.

| Group | Sample ID | Time Point | Eye | Retina Mass (g) | Amount of Diluent Added (μL) | Total Volume (μL)[1] | Calculated Concentration (ng/mL) | Calculated Concentration (ng/g) | Mean (ng/g) | SD | % CV |
|---|---|---|---|---|---|---|---|---|---|---|---|
| 1 | A | 24 hr | OD and OS | 0.01584 | 63 | 79 | 34.6 | 173 | 1210 | 1670 | 138 |
|   | B |  | OD and OS | 0.02249 | 90 | 112 | 736 | 3670 |  |  |  |
|   | C |  | OD and OS | 0.01744 | 70 | 87 | 29.2 | 146 |  |  |  |
|   | D |  | OD and OS | 0.01899 | 76 | 95 | 172 | 860 |  |  |  |
|   | A | 72 hr | OD and OS | 0.01395 | 56 | 70 | 81.5 | 409 | 570 | 172 | 30.2 |
|   | B |  | OD and OS | 0.01943 | 78 | 97 | 117 | 584 |  |  |  |
|   | C |  | OD and OS | 0.01514 | 61 | 76 | 96.0 | 482 |  |  |  |
|   | D |  | OD and OS | 0.01742 | 70 | 87 | 161 | 804 |  |  |  |
| 2 0.06 mg/mL Compound 1 in 4.5% mannitol, 10 mM acetic acid, 0.4% poloxamer 407, pH 4.5 | A-D | 72 hr | OD and OS | 0.06088 | 244 | 305 | 92.2 | 462 | NA | NA | NA |
|  | E-H | 72 hr | OD and OS | 0.04906 | 196 | 245 | 262 | 1310 | NA | NA | NA |

LLOQ = 20.0 ng/mL or 100 ng/g
Values < LLOQ use 0 for statistical determination
Footnote 1:
1.00 g/mL is assumed for rat retina tissue

TABLE 8

Concentrations of Compound 1 in Brown Norway rat vitreous humor.

| Group | Sample ID | Time Point | Eye | Calculated Concentration (ng/mL) | Vitreous Humor Weight (g)* | Calculated Concentration (μg/VH sample) | Mean (μg/VH sample) | SD | % CV |
|---|---|---|---|---|---|---|---|---|---|
| 1 0.06 mg/mL Compound 1 in 4.5% mannitol, 10 mM acetic acid, 0.4% poloxamer 407, pH 4.5 | A | 24 hr | OD and OS | 1780 | 0.05314 | 0.0946 | 0.157 | 0.0568 | 36.2 |
|  | B |  | OD and OS | 52.10 | 0.03262 | 0.170 |  |  |  |
|  | C |  | OD and OS | 4360 | 0.05262 | 0.229 |  |  |  |
|  | D |  | OD and OS | 3620 | 0.03768 | 0.136 |  |  |  |
|  | A | 72 hr | OD and OS | 1480 | 0.04818 | 0.0713 | 0.0994 | 0.0738 | 74.2 |
|  | B |  | OD and OS | 3740 | 0.05013 | 0.187 |  |  |  |
|  | C |  | OD and OS | 306 | 0.04681 | 0.0143 |  |  |  |
|  | D |  | OD and OS | 2350 | 0.05314 | 0.125 |  |  |  |
| 2 0.06 mg/mL Compound 1 in 4.5% mannitol, 10 mM acetic acid, 0.4% poloxamer 407, pH 4.5 | A | 72 hr | OD and OS | 3030 | 0.04931 | 0.149 | 0.127 | 0.0836 | 65.8 |
|  | B |  | OD and OS | 453 | 0.05496 | 0.0249 |  |  |  |
|  | C |  | OD and OS | 3590 | 0.05423 | 0.195 |  |  |  |
|  | D |  | OD and OS | 3610 | 0.05280 | 0.191 |  |  |  |
|  | E |  | OD and OS | 2910 | 0.04381 | 0.127 |  |  |  |
|  | F |  | OD and OS | 4070 | 0.05832 | 0.237 |  |  |  |
|  | G |  | OD and OS | 69.0 | 0.02919 | 0.00201 |  |  |  |
|  | H |  | OD and OS | 4300 | 0.01807 | 0.0867 |  |  |  |

LLOQ = 50.0 ng/mL
*assume density of 1.00 g/mL

Tissue Homogenization

Instructions for Homogenization of Vitreous Humor (VH) Unknowns

For each VH unknown or control blank: Weigh VH into a homogenization tube. Add 4 times the VH weight (mg) of ACN:water:1 M hydrochloric acid (70:20:10, v/v/v) (μL) to the homogenization tube. Add zirconium oxide beads, 2.8 and 1.4 mm size. Homogenize all samples on Precellys®: 5500 rpm, 3×30 second cycles, and 20 seconds between cycles, at a temperature between −10 to 0° C.

Instructions for Homogenization of Retina Ocular Tissue Standards

For each retina standard:

Weigh blank retina tissue into a homogenization tube.

Add 0.5 times the tissue weight (mg) of Retina Working Calibration Standard (μL) to the homogenization tube.

Add 3.5 times the tissue weight (mg) of ACN:water:1 M hydrochloric acid (70:20:10, v/v/v) (μL) to the homogenization tube.

Add zirconium oxide beads, 1.4 mm size.

Homogenize all samples on Precellys®: 5500 rpm, 3×30 second cycles, and 20 seconds between cycles, at a temperature between −10 to 0° C.

Instructions for Homogenization of Retina Tissue Blank Controls, and Unknowns

For each retina unknown or control blank:

Weigh retina tissue into a homogenization tube.

Add 4 times the tissue weight (mg) of ACN:water:1 M hydrochloric acid (70:20:10, v/v/v) (μL) to the homogenization tube.

Add zirconium oxide beads, 1.4 mm size.

Homogenize all samples on Precellys®: 5500 rpm, 3×30 second cycles, and 20 seconds between cycles, at a temperature between −10 to 0° C.

Preparation of Standards, Samples, and Blanks

Preparation of Calibration Stock and Working Standards

A stock calibration standard was prepared in dimethylsulfoxide (DMSO) at a concentration of 500 μg/mL for ONL-1204.

Working calibration standards were prepared for vitreous humor by serial dilution of working stock solution with ACN:wWater:1 M hydrochloric acid (70:20:10, v/v/v) over a range of 500 ng/mL to 200,000 ng/mL ONL-1204.

Working calibration standards were prepared for retina by serial dilution of working stock solution with acetonitrile:water:1 M hydrochloric acid (70:20:10) over a range of 100 ng/mL to 200,000 ng/mL ONL-1204.

Preparation of Standards, Unknowns, Blanks, and Blanks with Internal Standard for Vitreous Humor Analysis In a polypropylene tube, ten (10) μL (20 μL STD 11) of working calibration standard or stock was added to 90 μL (80 μL STD 11) control blank vitreous humor. For blanks and blanks with internal standard, 100 μL of control blank Bovine vitreous humor was added. Four hundred (400) μL of ACN:water:1 M hydrochloric acid (70:20:10, v/v/v) was added to each standard or blank.

One hundred (100) μL of each vitreous humor sample with ACN:formic acid (1000:1, v/v) was then aliquoted. One hundred (100) μL of DMSO:water:formic acid (50:40:10) was added to each vitreous humor sample. The samples were vortex mixed then centrifuged for 10 minutes at 14,000 rpm (4° C.). To 50.0 μL supernatant, 100 μL of working internal standard (50,000 ng/mL APi1887 in water) (water for the blank without internal standard), and 150 μL of water were added. The samples were then vortex mixed and transferred to an autosampler plate for analysis.

Preparation of Standards, Unknowns, Blanks, and Blanks with Internal Standard for Retina Analysis In a polypropylene tube, 50 μL of Brown Norway rat unknown homogenate, bovine control blank or calibration standard Bovine homogenate was added. Fifty (50) μL of DMSO:water:formic acid (50:40:10) was added to each sample. The samples were then vortex mixed and centrifuged for 10 minutes at 14,000 rpm (4° C.). Eighty (80) μL of each sample supernatant was then aliquoted to a 96-well autosampler plate. Forty (40) μL of working internal standard (5,000 ng/mL APi1887 in water) (water for the blank without internal standard), and 120 μL of water were added. The samples were then mixed with a multichannel pipette and analyzed.

Calculations

Percent Coefficient of Variation:

Used as an estimate of precision.

Percent Coefficient of Variation (% CV)=(Standard Deviation/average value)*100

Quadratic Least Squares Analysis:

The standard curve fit was determined using a quadratic equation with $1/x^2$ weighting:

$$y=ax^2+bx+c$$

where: y=peak area ratio of the calibration standards to internal standard x=concentration of the calibration standard a=quadratic coefficient of $x^2$ b=quadratic coefficient of x c=the constant as the y-intercept of the calibration curve Quadratic Analyte Concentration:

The concentration of analyte is calculated using the calibration curve parameters calculated above and then solving for the value of x.

Analysis

Figure 7:
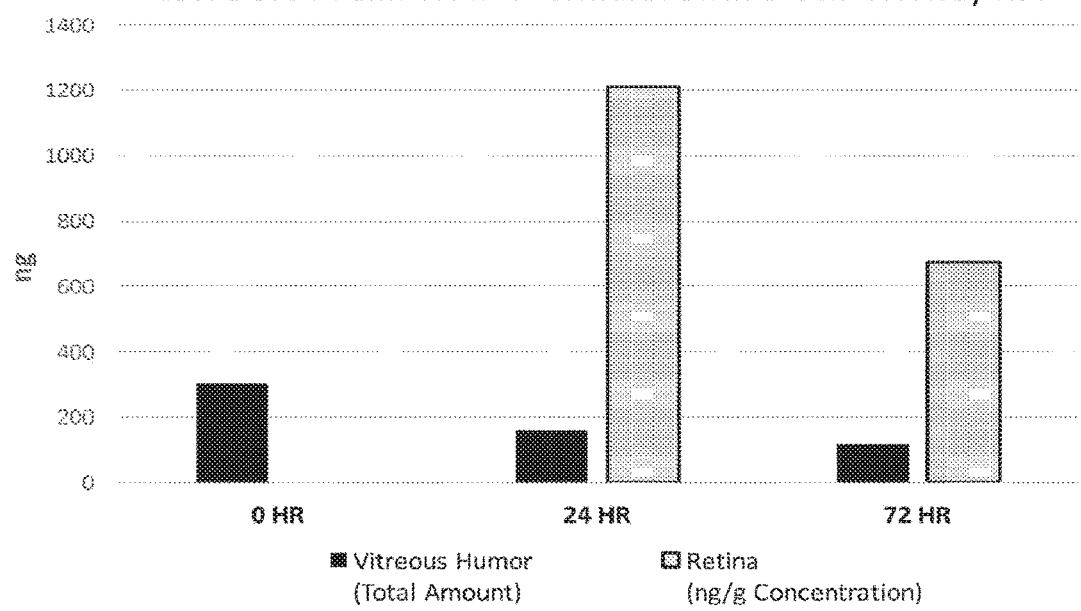
FIG. 7 shows total amounts of Compound 1 triacetate in the vitreous humor, (dark) and concentrations in the retinas, (light) of brown Norway rats 24 and 72 hours after a nominal injection of 300 ng of Compound 1 triacetate (5 µL of 0.06 mg/mL) in 4.5% mannitol, 10 mM acetic acid, 0.4% poloxamer (PX) 407, pH 4.5.

The globally averaged results are shown in FIG. 7. For Group 1 both eyes from each animal were combined for a single analysis. In Group 2 both eyes were combined from 4 animals to make samples. Concentrations for the pooled retina in Group 2 were 462 and 1310 ng/g for the A-D and E-H samples respectively. Analysis of vitreous humor for Compound 1 was conducted using combined samples from each eye for each animal in Groups 1 and 2. When normalized by weight of the VH collected, a theoretical total of Compound 1 was calculated. The total amount of Compound 1 injected into each rat eye was 0.3 μg (0.06 mg/mL*5 μL)). Because of the different ways the 72 hour data was collected, standard error was not calculated. The dark bars represent the amount of Compound 1 triacetate in the vitreous humor of each eye, with the t=0 bar representing the intended dose of 300 ng, and the light bars represent the concentration of Compound 1 in the retina expressed in ng/g. In the first 24 hours, about half the drug cleared the VH, but the terminal half-life was clearly on the order of several days. Meanwhile, retinal concentrations were above 1 μg/g at 24 hrs, and have only about 40% by 72 hrs. This suggests that the rat retina will be exposed to the drug in readily detectable amounts for at least a week.

Retinal concentrations of Compound 1 ranged from 146 to 3670 ng/g for the Group 1 24 hour samples, and from 409 to 804 ng/g in the Group 1 72 hour samples. Mean Compound 1 remaining in the VH for Group 1 was 0.157 and 0.0994 μg/sample at the 24 hour and 72 hour time points respectively. Mean Compound 1 remaining in the VH for Group 2 samples at 72 hours was 0.127 μg/sample. The data indicates that substantial amounts of intact drug remain 72 hours post-administration.

Example 10: In Vivo Efficacy of Compound 1

Briefly, rodents were anesthetized with a 50:50 mix of ketamine (100 mg/mL) and xylazine (20 mg/mL), and pupils were dilated with topical phenylephrine (2.5%) and tropicamide (1%). A 20-gauge microvitreoretinal blade (Walcott Scientific, Marmora, N.J.) was used to create a sclerotomy 2 mm posterior to the limbus, carefully avoiding lens damage.

Under direct visualization through an operating microscope, a subretinal injector (Glaser, 32-gauge tip; BD Ophthalmic Systems, Sarasota, Fla.) was introduced through the sclerotomy into the vitreous cavity and then through a peripheral retinotomy into the subretinal space. Sodium hyaluronate (10 mg/mL) was slowly injected to detach the neurosensory retina from the underlying retinal pigment epithelium.

In all experiments, approximately one-third to one-half of the superonasal neurosensory retina was detached. In all animals, detachments were created in the same location to allow for direct comparison of retinal cell counts. Detachments were created in the left eye, leaving the right eye as the control.

In some eyes, wild-type Met-12 (HHIYLGAVNYIY, 5 µg in DMSO) as its trihydrochloride salt was given as a positive control, and in other eyes, Compound 1 (0.5, 1.0, 5.0 or 10 µg in DMSO) as its trihydrochloride salt, or vehicle (dimethyl sulfoxide [DMSO]) was injected into the subretinal space in the area of the detachment in a 5-µL volume using a Hamilton syringe (Hamilton Company, Reno, Nev.) immediately after the creation of the detachment.

After three days rats were euthanized, retinas were excised, fixed, sectioned, and stained for TUNEL assays. Areas of detached retina were counted for number of apoptotic cells. Each experiment involved 4 fields from each of 4 sections obtained from 5 or 6 retinas for each dosing group. The results are shown in FIG. 8.

Figure 8:
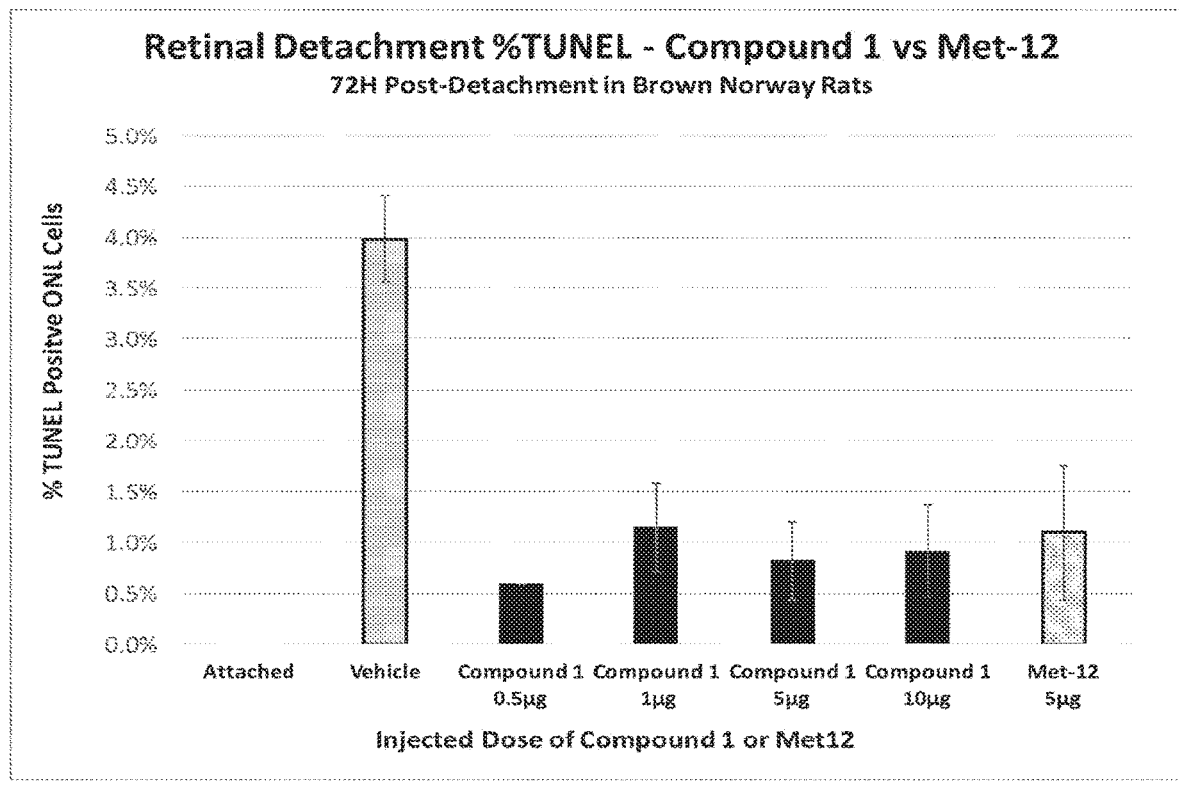
FIG. 8 shows a bar graph depicting the number of apoptotic cells after 72 hrs following in vivo treatments of detached retinas in rats with Met-12 trihydrochloride (light stripe) (5 µg in 5 µL DMSO), and Compound 1 trihydrochloride (dark) (0.5, 1.0, 5 and 10 µg in 5 µL DMSO), or DMSO vehicle (light). The LHS bar is undetached control retina with no injection.

As shown in FIG. 8, control attached retinas showed no apoptocic cells, whereas DMSO control retinas have approximately 4% of cells staining for TUNEL, and the positive control Met-12 (5 µg) with just over 1% positive for TUNEL. Compound 1 trihydrochloride salt treatment led to 0.58% at 0.5 µg, 1.14% at 1 µg, 0.82% at 5 µg, and 0.9% at 10 µg. Based on considerable experience with the model, the results for Compound 1 are considered approximately equivalent with each other and with the Met-12.5 µg positive control. Thus unexpectedly, Compound 1 trihydrochloride salt is much more efficacious than Met-12 trihydrochloride salt in this in vivo model.

Example 11: Efficacy Study

Using the same rodent retinal detachment model as in Example 10, the highly efficacious 5 µg dose of Compound 1 in DMSO was compared with the same dose, and a 1 µg dose of Compound 1 in two different formulations.

Figure 9:
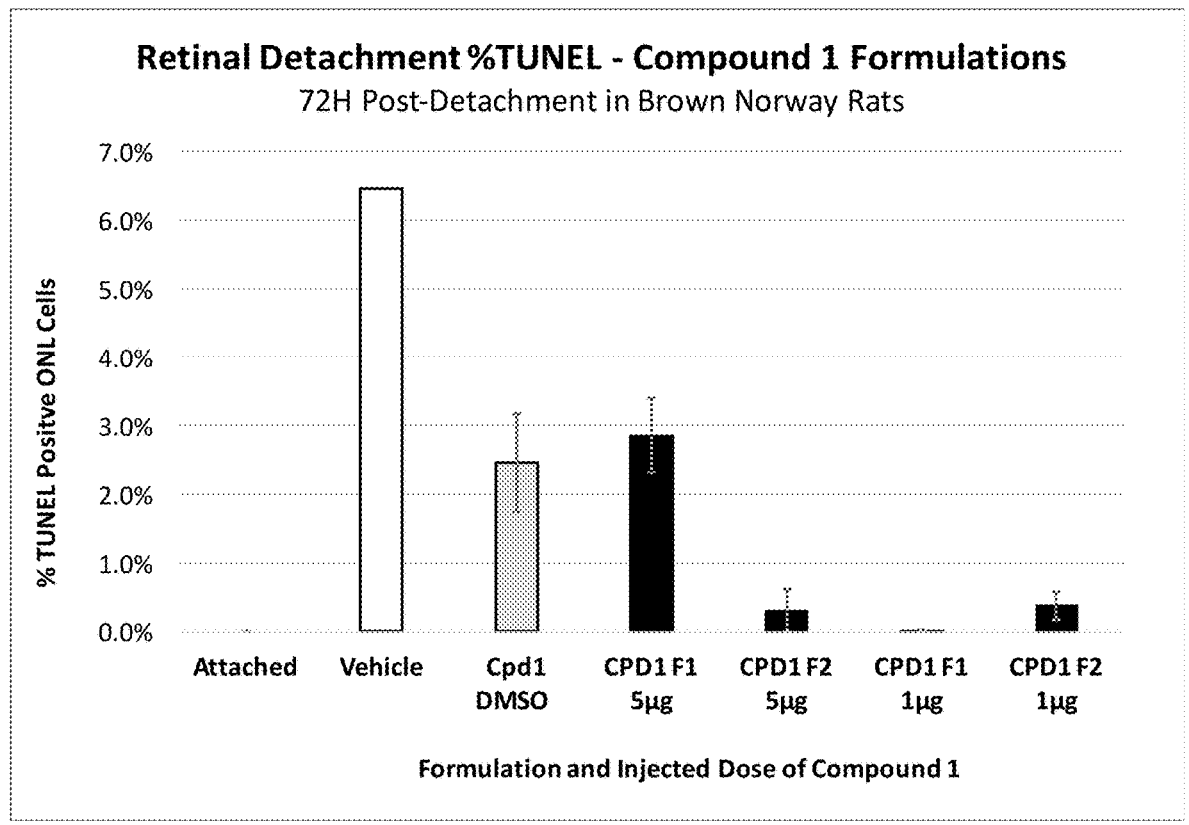
FIG. 9 shows a bar graph depicting the number of apoptotic cells after 72 hrs following in vivo treatments of detached retinas in rats with Compound 1 trihydrochloride (1.0 and 5 µg in 5 µL of F1 or F2), against the same (5 µg in 5 µL) in DMSO or DMSO vehicle (gray). The LHS bar is undetached control retina with no injection. F1 (5/1 µg) is 1.0/0.2 mg/mL Compound 1 trihydrochloride in 3% PG/3% PS-20 at pH 4.0 (black), and F2 (5/1 µg) is 1.0/0.2 mg/mL Compound 1 trihydrochloride in 2% PG/2% PX-407 at pH 4.0 (vertical stripes).
Figure 10:
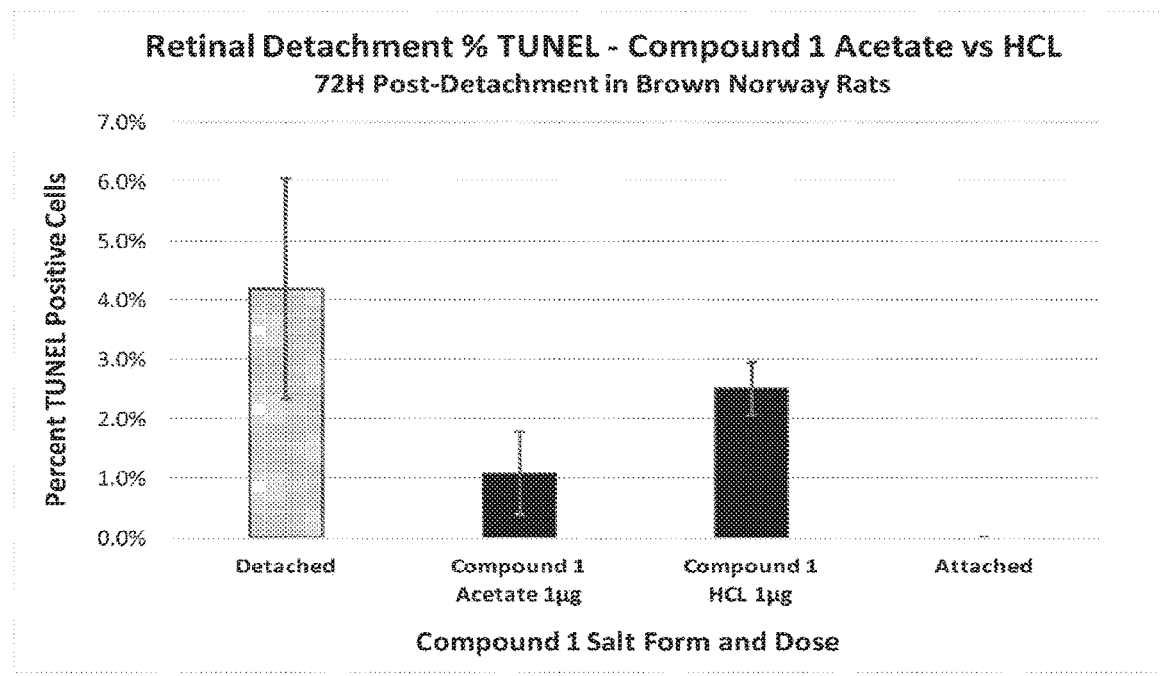
FIG. 10 shows a bar graph depicting the percent of apoptotic cells after 72 hrs following in vivo treatments of detached retinas in rats. Bar 1 is a vehicle control in detached retinas. Bar 2 with 1 µg of Compound 1 triacetate as an 0.2 mg/mL DMSO solution. Bar 3 is 1 µg of Compound 1 trihydrochloride as an 0.2 mg/mL DMSO solution. Bar 4 is undetached control retina with no injection.

The first formulation was a 1.0 or 0.2 mg/mL solution of Compound 1 trihydrochloride in 3% propylene glycol and 3% PS-20 at pH 4.0, and the second formulation was the same concentrations of Compound 1 in a 2% propylene glycol 2% poloxamer 407 solution, also at pH 4. The results are shown in FIG. 9.

The attached control retinas showed no apoptotic cells whereas the untreated detachments showed approximately 6.5% apoptotic cells as measured at this time point. Compound 1 in DMSO reduced that to 2.5%, and the 5 µg PG/PS-20 was of similar potency reducing the apoptotic cells to 2.9%. However the PG/PX formulation was considerably better at that concentration reducing the apoptotic cells to 0.3% at 5 µg. At 1 µg the PG/PX formulation reduced apoptotic cells to 0.4%, but the PG/PS-20 1 µg dose produced an even greater lowering to 0.01%. The data demonstrates that not only can micellar formations work, but that Compound 1 trihydrochloride salt can be even more potent in them than when it is formulated in DMSO.

Example 12: Efficacy Study

Using the same rodent retinal detachment model as in Example 10, Compound 1 trihydrochloride salt in DMSO (1 µg) was used as the positive control. The negative control was a test vehicle under evaluation (0.4% Poloxamer, 4.5% mannitol, 10 mM acetic acid at pH 4.5.) Compound 1 triacetate salt in DMSO (1 µg) was compared to the trihydrochloride salt at the same dose.

The attached retinas (Bar 4) had no apoptotic cells, whereas vehicle treated detached retinas (Bar 1) showed 4.2% apoptotic cells, which suggests no activity, as it is within the historic range for untreated retinal detachments (See example 10). The Compound 1 trihydrochloride salt (DMSO) gave 2.4% apoptotic cells, whereas the triacetate salt (DMSO) gave only 1.2%, demonstrating that the switch from hydrochloride to acetate salts does not have negative effects, and quite possibly positive effects on efficacy.

All publications and patents mentioned in the present application and/or listed below are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

Although the present invention has been described in considerable detail with reference to certain embodiments thereof, other embodiments are possible without departing from the present invention. The spirit and scope of the appended claims should not be limited, therefore, to the description of the preferred embodiments contained herein. All embodiments that come within the meaning of the claims, either literally or by equivalence, are intended to be embraced therein.

Furthermore, the advantages described above are not necessarily the only advantages of the invention, and it is not necessarily expected that all of the described advantages will be achieved with every embodiment of the invention.

The invention claimed is:

1. A pharmaceutical composition comprising an excipient and a compound having the formula:

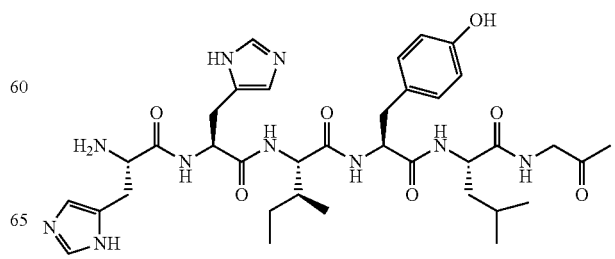

-continued

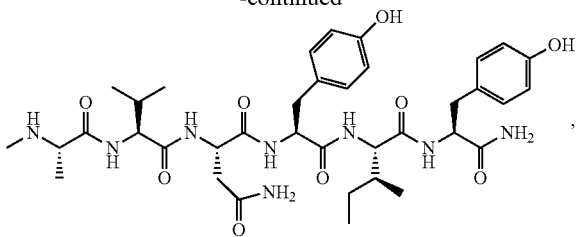

or a pharmaceutically acceptable salt thereof.

2. The composition of claim 1, wherein the composition is formulated for intraocular injection, intravitreal injection, or periocular injection.

3. The composition of claim 1, wherein the compound is present in the composition at a concentration of 0.5 mg/mL to 2.0 mg/mL.

4. The composition of claim 1, wherein the excipient comprises a tonicity-adjusting agent, a surfactant, a buffering agent, or a combination of any one or more thereof.

5. The composition of claim 4, wherein the excipient is a surfactant and the surfactant is present in the composition at a concentration of 0.01% to 20% w/w.

6. The composition of claim 1, wherein the excipient is a buffering agent and the composition is buffered at a pH of 2.5 to 6.0.

7. The composition of claim 1, wherein the composition is formulated for ocular use, comprises the compound in a concentration of 0.5 mg/mL to 2.0 mg/mL, and is buffered at a pH of 2.5 to 6.0.

8. A method for treating retinal detachment in an individual having a detached retina, the method comprising administering to the individual a therapeutically effective amount of a compound having the formula:

9. The method of claim 8, wherein the compound is administered in an amount of 25 µg to 200 µg.

10. The method of claim 8, wherein the compound is administered in a pharmaceutical composition and the pharmaceutical composition comprises the compound in a concentration of 0.5 mg/mL to 2.0 mg/mL.

11. The method of claim 10, wherein the pharmaceutical formulation is administered in a volume ranging from 10 µL to 500 µL.

12. The method of claim 8, wherein the method consists of administering the compound to the individual a single time.

13. The method of claim 8, wherein the method comprises administering the compound to the individual multiple times.

14. The method of claim 8, wherein the compound is administered by intraocular injection, intravitreal injection, or periocular injection.

15. The method of claim 8, wherein (a) the compound is administered in an amount of 25 µg to 200 µg, (b) the compound is administered in a pharmaceutical composition and the pharmaceutical composition comprises the compound in a concentration of 0.5 mg/mL to 2.0 mg/mL; and (c) the compound is administered by intraocular injection, intravitreal injection, or periocular injection.

16. A method for treating macular degeneration in an individual in need thereof, the method comprising administering to the individual a therapeutically effective amount of a compound having the formula:

(Formula I)

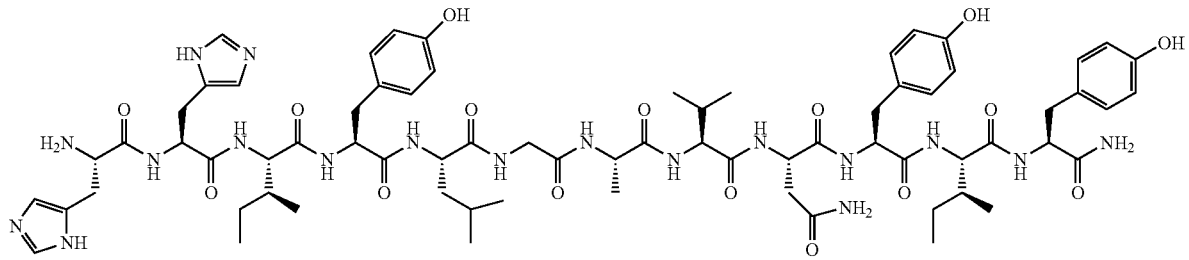

or a pharmaceutically acceptable salt thereof.

(Formula I)

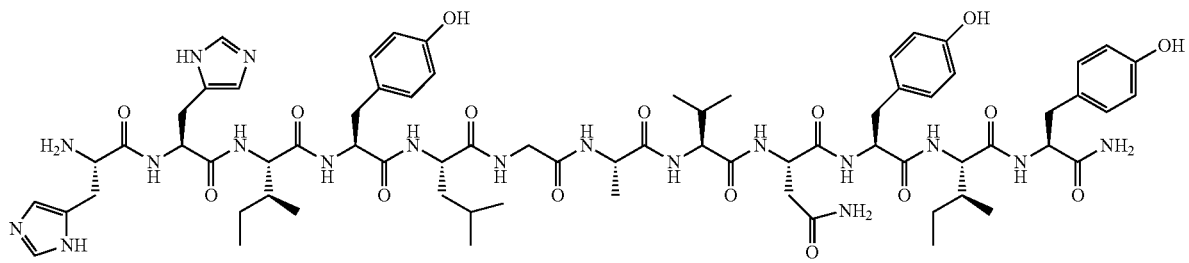

or a pharmaceutically acceptable salt thereof.

17. The method of claim 16, wherein the compound is administered by intraocular injection, intravitreal injection, or periocular injection.

18. The method of claim 16, wherein the compound is administered in an amount of 25 μg to 200 μg.

19. The method of claim 16, wherein the compound is administered in a pharmaceutical composition and the pharmaceutical composition comprises the compound in a concentration of 0.5 mg/mL to 2.0 mg/mL.

20. The method of claim 19, wherein the pharmaceutical formulation is administered in a volume ranging from 10 μL to 500 μL.

21. The method of claim 16, wherein the macular degeneration is age-related macular degeneration, dry-form macular degeneration, wet macular degeneration, non-exudative macular degeneration, or exudative macular degeneration.

22. The method of claim 16, wherein treating macular degeneration comprises treating an atrophy associated therewith.

* * * * *